(12) United States Patent
Wang et al.

(10) Patent No.: US 8,937,300 B2
(45) Date of Patent: Jan. 20, 2015

(54) TRIARYLAMINE COMPOUNDS FOR USE IN ORGANIC LIGHT-EMITTING DIODES

(75) Inventors: Ying Wang, Wilmington, DE (US);
Weishi Wu, Landenberg, PA (US);
Kerwin D. Dobbs, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 222 days.

(21) Appl. No.: 12/907,067

(22) Filed: Oct. 19, 2010

(65) Prior Publication Data

US 2011/0253986 A1     Oct. 20, 2011

Related U.S. Application Data

(60) Provisional application No. 61/362,427, filed on Jul. 8, 2010, provisional application No. 61/252,808, filed on Oct. 19, 2009.

(51) Int. Cl.
| | | |
|---|---|---|
| *H01L 29/08* | (2006.01) | |
| *C09K 11/06* | (2006.01) | |
| *C07C 211/54* | (2006.01) | |
| *H01L 51/00* | (2006.01) | |
| *H05B 33/20* | (2006.01) | |

(52) U.S. Cl.
CPC .............. *C09K 11/06* (2013.01); *C07C 211/54* (2013.01); *H01L 51/0059* (2013.01); *H05B 33/20* (2013.01); *C09K 2211/1007* (2013.01); *C09K 2211/1014* (2013.01)
USPC ...... 257/40; 257/E51.024; 564/307; 564/315; 252/301.16

(58) Field of Classification Search
CPC ....... C07C 211/54; C09K 11/06; H01L 51/54
USPC ................... 257/40, E51.024; 564/307, 315; 252/301.16
See application file for complete search history.

(56) References Cited

U.S. PATENT DOCUMENTS

| | | |
|---|---|---|
| 3,265,496 A | 8/1966 | Fox |
| 3,955,978 A | 5/1976 | Rochlitz et al. |
| 4,047,948 A | 9/1977 | Horgan |
| 4,047,949 A | 9/1977 | Horgan |
| 4,086,209 A | 4/1978 | Hara et al. |
| 4,115,116 A | 9/1978 | Stolka et al. |
| 4,127,412 A | 11/1978 | Rule et al. |
| 4,233,384 A | 11/1980 | Turner et al. |
| 4,265,990 A | 5/1981 | Stolka et al. |
| 4,299,897 A | 11/1981 | Stolka et al. |
| 4,322,487 A | 3/1982 | Merrill et al. |

(Continued)

FOREIGN PATENT DOCUMENTS

| | | |
|---|---|---|
| DE | 196 43 097 A1 | 4/1998 |
| DE | 101 09 463 A1 | 10/2002 |

(Continued)

OTHER PUBLICATIONS

Gustafsson et al., Nature, Flexible Light Emitting Diodes Made From Soluble Conducting Polymers, 1992, V357, pp. 477-479.

(Continued)

*Primary Examiner* — Caleb Henry

(57) ABSTRACT

This invention relates to triarylamine compounds that are useful in electronic applications. It also relates to electronic devices in which the active layer includes such a compound.

14 Claims, 2 Drawing Sheets

(56) References Cited

U.S. PATENT DOCUMENTS

| | | | |
|---|---|---|---|
| 4,346,158 A | 8/1982 | Pai et al. | |
| 4,504,564 A | 3/1985 | Pai et al. | |
| 4,517,354 A | 5/1985 | D'Alelio | |
| 4,665,000 A | 5/1987 | Tokoli et al. | |
| 4,714,779 A | 12/1987 | Turner et al. | |
| 4,801,517 A | 1/1989 | Frechet et al. | |
| 4,898,800 A * | 2/1990 | Shimada et al. | 430/58.65 |
| 4,933,053 A | 6/1990 | Tieke | |
| 4,933,245 A | 6/1990 | Akasaki et al. | |
| 4,937,165 A | 6/1990 | Ong et al. | |
| 4,946,754 A | 8/1990 | Ong et al. | |
| 5,126,214 A | 6/1992 | Tokailin et al. | |
| 5,130,481 A | 7/1992 | Khanna et al. | |
| 5,155,200 A | 10/1992 | Limburg et al. | |
| 5,237,045 A | 8/1993 | Burchill et al. | |
| 5,262,261 A * | 11/1993 | Kikuchi et al. | 430/58.65 |
| 5,449,564 A | 9/1995 | Nishio et al. | |
| 5,487,953 A | 1/1996 | Shirota et al. | |
| 5,554,450 A * | 9/1996 | Shi et al. | 428/690 |
| 5,616,442 A * | 4/1997 | Kanemaru et al. | 430/83 |
| 5,652,067 A | 7/1997 | Ito et al. | |
| 5,677,097 A | 10/1997 | Nukada et al. | |
| 5,681,664 A | 10/1997 | Tamano et al. | |
| 5,728,801 A | 3/1998 | Wu et al. | |
| 5,789,128 A | 8/1998 | Adachi et al. | |
| 5,792,557 A | 8/1998 | Nakaya et al. | |
| 5,814,244 A * | 9/1998 | Kreuder et al. | 252/301.16 |
| 5,817,739 A | 10/1998 | Nukada et al. | |
| 5,846,681 A | 12/1998 | Yu et al. | |
| 5,853,906 A * | 12/1998 | Hsieh | 428/690 |
| 5,891,587 A | 4/1999 | Hu et al. | |
| 5,929,194 A | 7/1999 | Woo et al. | |
| 5,962,631 A | 10/1999 | Woo et al. | |
| 5,994,573 A | 11/1999 | Tachikawa et al. | |
| 6,020,426 A | 2/2000 | Yamaguchi et al. | |
| 6,043,370 A * | 3/2000 | Kubo et al. | 546/257 |
| 6,107,439 A | 8/2000 | Yanus et al. | |
| 6,107,452 A | 8/2000 | Miller et al. | |
| 6,132,913 A | 10/2000 | Fuller et al. | |
| 6,143,452 A | 11/2000 | Sakimura et al. | |
| 6,271,356 B1 * | 8/2001 | Shimada et al. | 534/755 |
| 6,277,504 B1 | 8/2001 | Koch et al. | |
| 6,287,713 B1 | 9/2001 | Heuer et al. | |
| 6,294,273 B1 | 9/2001 | Heuer et al. | |
| 6,303,238 B1 | 10/2001 | Thompson et al. | |
| 6,316,130 B1 | 11/2001 | Heuer | |
| 6,322,908 B1 | 11/2001 | Oda | |
| 6,361,885 B1 | 3/2002 | Chou | |
| 6,368,731 B1 | 4/2002 | Heuer et al. | |
| 6,376,106 B1 | 4/2002 | Uchida et al. | |
| 6,376,694 B1 | 4/2002 | Uchida et al. | |
| 6,376,695 B1 | 4/2002 | Kushibiki et al. | |
| 6,503,643 B1 | 1/2003 | Heuer et al. | |
| 6,517,957 B1 | 2/2003 | Senoo et al. | |
| 6,534,200 B1 | 3/2003 | Heuer et al. | |
| 6,541,128 B2 | 4/2003 | Wehrmann et al. | |
| 6,558,818 B1 | 5/2003 | Samuel et al. | |
| 6,630,566 B1 * | 10/2003 | Allen et al. | 528/422 |
| 6,646,164 B2 | 11/2003 | Uemura et al. | |
| 6,670,645 B2 | 12/2003 | Grushin et al. | |
| 6,689,491 B1 | 2/2004 | Nii et al. | |
| 6,723,455 B2 * | 4/2004 | Ueda et al. | 428/690 |
| 6,800,722 B2 | 10/2004 | Pei et al. | |
| 6,830,832 B2 | 12/2004 | Oguma et al. | |
| 6,852,355 B2 | 2/2005 | Blanchet-Fincher | |
| 6,852,429 B1 | 2/2005 | Li et al. | |
| 6,875,524 B2 | 4/2005 | Hatwar et al. | |
| 6,905,785 B2 | 6/2005 | Noguchi et al. | |
| 6,962,758 B2 * | 11/2005 | Chen et al. | 428/690 |
| 7,023,013 B2 | 4/2006 | Ricks et al. | |
| 7,166,010 B2 * | 1/2007 | Lamansky et al. | 445/24 |
| 7,173,131 B2 | 2/2007 | Saitoh et al. | |
| 7,258,932 B2 * | 8/2007 | Noguchi et al. | 428/690 |
| 7,273,953 B2 * | 9/2007 | Kubo | 564/405 |
| 7,358,409 B2 | 4/2008 | Saitoh et al. | |
| 7,375,250 B2 | 5/2008 | Saitoh et al. | |
| 7,402,681 B2 | 7/2008 | Ong et al. | |
| 7,491,450 B2 | 2/2009 | Okinaka et al. | |
| 7,527,903 B2 * | 5/2009 | Carmichael et al. | 430/58.8 |
| 7,569,728 B2 * | 8/2009 | Smith et al. | 564/315 |
| 7,598,010 B2 * | 10/2009 | Kita et al. | 430/58.85 |
| 7,629,059 B2 * | 12/2009 | Akashi et al. | 428/690 |
| 7,651,788 B2 | 1/2010 | Seo et al. | |
| 7,709,104 B2 | 5/2010 | Saitoh et al. | |
| 7,771,843 B2 | 8/2010 | Suh et al. | |
| 7,960,587 B2 | 6/2011 | Herron et al. | |
| 8,039,126 B2 * | 10/2011 | Stossel et al. | 428/690 |
| 8,043,725 B2 * | 10/2011 | Kobata et al. | 428/690 |
| 2001/0017155 A1 | 8/2001 | Bellmann et al. | |
| 2001/0019782 A1 | 9/2001 | Igarashi et al. | |
| 2002/0050597 A1 | 5/2002 | Hirose et al. | |
| 2002/0051918 A1 * | 5/2002 | Miyamoto et al. | 430/58.65 |
| 2002/0055014 A1 | 5/2002 | Okada et al. | |
| 2002/0057050 A1 | 5/2002 | Shi | |
| 2002/0076576 A1 | 6/2002 | Li | |
| 2003/0038287 A1 | 2/2003 | Suzuki et al. | |
| 2003/0064308 A1 | 4/2003 | Kita et al. | |
| 2003/0099862 A1 | 5/2003 | O'Neill et al. | |
| 2003/0146443 A1 * | 8/2003 | Yamazaki et al. | 257/80 |
| 2003/0162053 A1 | 8/2003 | Marks et al. | |
| 2003/0207152 A1 | 11/2003 | Hsieh et al. | |
| 2003/0224205 A1 | 12/2003 | Li et al. | |
| 2003/0225234 A1 | 12/2003 | Jaycox et al. | |
| 2003/0232264 A1 | 12/2003 | Tokarski et al. | |
| 2004/0004433 A1 * | 1/2004 | Lamansky et al. | 313/506 |
| 2004/0029133 A1 | 2/2004 | Herrnstadt | |
| 2004/0102577 A1 | 5/2004 | Hsu et al. | |
| 2004/0106003 A1 | 6/2004 | Chen et al. | |
| 2004/0127637 A1 | 7/2004 | Hsu et al. | |
| 2004/0189190 A1 | 9/2004 | Suzuri et al. | |
| 2004/0254297 A1 | 12/2004 | Hsu et al. | |
| 2005/0031898 A1 | 2/2005 | Li et al. | |
| 2005/0064237 A1 | 3/2005 | Kato et al. | |
| 2005/0067951 A1 | 3/2005 | Richter et al. | |
| 2005/0073249 A1 | 4/2005 | Morii et al. | |
| 2005/0158577 A1 | 7/2005 | Ishibashi et al. | |
| 2005/0184287 A1 | 8/2005 | Herron et al. | |
| 2005/0186106 A1 | 8/2005 | Li et al. | |
| 2005/0205860 A1 | 9/2005 | Hsu et al. | |
| 2005/0227465 A1 | 10/2005 | Smith et al. | |
| 2005/0260448 A1 | 11/2005 | Lin et al. | |
| 2006/0003258 A1 | 1/2006 | Vargas et al. | |
| 2006/0033421 A1 | 2/2006 | Matsuura et al. | |
| 2006/0052641 A1 | 3/2006 | Funahashi | |
| 2006/0063852 A1 | 3/2006 | Iwata et al. | |
| 2006/0099451 A1 * | 5/2006 | Igarashi | 428/690 |
| 2006/0113528 A1 | 6/2006 | Okinaka et al. | |
| 2006/0121312 A1 | 6/2006 | Yamada et al. | |
| 2006/0159838 A1 | 7/2006 | Kowalski et al. | |
| 2006/0257767 A1 | 11/2006 | Tong et al. | |
| 2006/0267488 A1 | 11/2006 | Saitoh et al. | |
| 2007/0063638 A1 | 3/2007 | Tokairin et al. | |
| 2007/0114917 A1 | 5/2007 | Funahashi et al. | |
| 2007/0194698 A1 * | 8/2007 | Herron et al. | 313/504 |
| 2007/0255076 A1 | 11/2007 | Ito et al. | |
| 2007/0292713 A9 | 12/2007 | Dobbs et al. | |
| 2007/0298530 A1 | 12/2007 | Feehery | |
| 2008/0039581 A1 * | 2/2008 | Brown et al. | 524/796 |
| 2008/0071049 A1 | 3/2008 | Radu et al. | |
| 2008/0191614 A1 | 8/2008 | Kim et al. | |
| 2008/0233433 A1 | 9/2008 | Igarashi et al. | |
| 2008/0255387 A1 * | 10/2008 | Masaki et al. | 564/270 |
| 2008/0286605 A1 | 11/2008 | Takeda | |
| 2008/0305418 A1 * | 12/2008 | Hamasaki et al. | 430/78 |
| 2009/0035017 A1 * | 2/2009 | Tada et al. | 399/159 |
| 2009/0058279 A1 | 3/2009 | Takeda | |
| 2009/0206327 A1 | 8/2009 | Radu et al. | |
| 2009/0232551 A1 | 9/2009 | Nagao et al. | |
| 2009/0295274 A1 * | 12/2009 | Hwang et al. | 313/504 |
| 2009/0309070 A1 | 12/2009 | Ogata et al. | |
| 2010/0187505 A1 * | 7/2010 | Stoessel et al. | 257/40 |

(56) References Cited

U.S. PATENT DOCUMENTS

2010/0187983 A1     7/2010   Herron et al.
2010/0256328 A1*   10/2010   Heckmeier et al. ........... 528/396

FOREIGN PATENT DOCUMENTS

| | | |
|---|---|---|
| DE | 10 2004020046 | 7/2005 |
| EP | 0372979 | 6/1990 |
| EP | 650955 B1 | 8/1998 |
| EP | 1 154 331 A1 | 11/2001 |
| EP | 1191612 | 3/2002 |
| EP | 1191612 A2 | 3/2002 |
| EP | 1191614 | 3/2002 |
| EP | 1191614 A2 | 3/2002 |
| EP | 1215945 | 6/2002 |
| EP | 1227529 | 7/2002 |
| EP | 1277824 A1 | 1/2003 |
| EP | 1 284 258 A2 | 2/2003 |
| EP | 1394617 A2 | 3/2004 |
| EP | 1398340 A1 | 3/2004 |
| EP | 1414081 A2 | 4/2004 |
| EP | 1 464 691 A | 10/2004 |
| EP | 1586616 | 10/2005 |
| EP | 2067766 A1 | 6/2009 |
| EP | 2067767 A1 | 6/2009 |
| EP | 2080762 | 7/2009 |
| GB | 2334959 | 8/1999 |
| JP | 05032596 A | 2/1993 |
| JP | 05112509 A | 5/1993 |
| JP | 08278642 A | 10/1996 |
| JP | 08292586 A | 11/1996 |
| JP | 10251633 A | 9/1998 |
| JP | 10265773 A | 10/1998 |
| JP | 10284252 A | 10/1998 |
| JP | 11327181 A | 11/1999 |
| JP | 2000143786 A | 5/2000 |
| JP | 2000297068 A | 10/2000 |
| JP | 2001089428 A | 4/2001 |
| JP | 2002080570 A | 3/2002 |
| JP | 2002 212150 A | 7/2002 |
| JP | 2003253001 A | 9/2003 |
| JP | 2003277333 | 10/2003 |
| JP | 2004 030942 A1 | 1/2004 |
| JP | 2004010550 A | 1/2004 |
| JP | 2004176024 A | 6/2004 |
| JP | 2004184569 A | 7/2004 |
| JP | 2005054077 | 3/2005 |
| JP | 2006151844 A | 6/2006 |
| JP | 2006219392 A | 8/2006 |
| JP | 2009016719 A | 1/2009 |
| JP | 2009091304 A | 4/2009 |
| JP | 2009198566 A | 9/2009 |
| JP | 2009229776 A | 10/2009 |
| KR | 1020090046731 A | 5/2009 |
| KR | 1020090086015 A | 8/2009 |
| KR | 1020090086920 A | 8/2009 |
| KR | 1020090093897 A | 9/2009 |
| WO | 9954385 A1 | 10/1999 |
| WO | 00/53565 A1 | 9/2000 |
| WO | 0055927 A1 | 9/2000 |
| WO | 00/70655 A2 | 11/2000 |
| WO | 0070655 | 11/2000 |
| WO | 0141512 | 6/2001 |
| WO | 0141512 A1 | 6/2001 |
| WO | WO 01/49769 A1 | 7/2001 |
| WO | 02/02714 A2 | 1/2002 |
| WO | 0202714 | 1/2002 |
| WO | WO02/01653 A | 1/2002 |
| WO | 02/15645 A1 | 2/2002 |
| WO | 03008424 A1 | 1/2003 |
| WO | 03-063555 | 7/2003 |
| WO | 03091688 A2 | 11/2003 |
| WO | WO 2004/005406 A | 1/2004 |
| WO | 2004-016710 | 2/2004 |
| WO | 2004 025748 | 3/2004 |
| WO | 2004106409 A1 | 12/2004 |
| WO | 03-040257 | 5/2005 |
| WO | 2005-052027 | 6/2005 |
| WO | 2005049546 A1 | 6/2005 |
| WO | 2005049548 A1 | 6/2005 |
| WO | 2005049689 A2 | 6/2005 |
| WO | 2005080525 A2 | 9/2005 |
| WO | 2006043087 A1 | 4/2006 |
| WO | 2006072002 A2 | 7/2006 |
| WO | 2006072015 A2 | 7/2006 |
| WO | 2006086684 A1 | 8/2006 |
| WO | 2006088556 | 8/2006 |
| WO | 2007-021117 | 2/2007 |
| WO | 2007076146 A2 | 7/2007 |
| WO | 2007079103 A2 | 7/2007 |
| WO | 2007100096 A1 | 9/2007 |
| WO | 2007105917 A1 | 9/2007 |
| WO | 2007108666 A1 | 9/2007 |
| WO | 2008024378 A2 | 2/2008 |
| WO | 2008024379 A2 | 2/2008 |
| WO | 2008149968 A1 | 12/2008 |
| WO | 2009-018009 | 2/2009 |
| WO | 2009028902 A2 | 3/2009 |
| WO | 2009055628 A1 | 4/2009 |
| WO | 2009067419 A1 | 5/2009 |

OTHER PUBLICATIONS

Othmer, K., Encyclopedia of chemical Technology, 1996, 18 (4$^{th}$ Ed), 837-860.

Markus, Electronics and Nucleonics Dictionary, 470 and 476, Mcgraw-Hill Inc. 1966 (Book Not Included).

Yersin et al., Triplet Emitters for Organic Light-Emitting Diodes: Basic Properties Highly Efficient OLDES With Phosphorescent Materials, 2008 (Book Not Included).

Shih et al., Novel Carbazole/Fluorene Hybrids: Host Materials for Blue Phosphorescent OLEDS, Organic Letters, 2006, vol. 8, pp. 2799-2802.

Schaugaard, Novel Host Materials for Highly Efficient Blue Emitting OLEDS, Edmonds Community College, pp. 71-73.

Kim et al., New Host Materials Containing Carbazole and Naphthyl Moieties for Green Dopant in Phosphorescence Organic Light-Emitting Diodes, Korean Chem Soc, 2008, vol. 29, pp. 2270-2272.

Ge et al., Solution Processible Bipolar Triphenylamine Benzimidazole Derivatives for Highly Efficient Single Layer Organic Light Emitting Diodes, Chem Mater, 2008, vol. 20, pp. 2532-2537.

Borsenberger et al., Hole Transport in 1,1-Bis (Di-4-Tolylamino) Phenyl) Cyclohexane (TAPC) Doped Poly(Styrene)S, Jphysical Chem, 1993, vol. 97, pp. 8250-8253.

Mutaguchi, D. et al., Development of a new class of hole-transporting and emitting vinyl polymers and their application in organic electroluminescent devices, Organic Electronics, 2003, 4, 49-59.

Y. Wang, Dramatic Effects of Hole Transport Layer on the Efficiency of Iridium-Based Organic Light-Emitting Diodes, Appl. Phys. Letters, 2004, vol. 85, pp. 4848.

CRC Handbook of Chemistry and Physics, 81st Edition, 2000 (Book Not Included).

Wang, Photoconductive Materials. Photoconductive Polymers, Kirk-Othmer Encyl. of Chemical Technology, 4th Ed., 1996, vol. 18:837-860 (Book Not Included).

International Preliminary Report on Patentability, International Bureau of WIPO, Geneva CH, by Agnes Wittmann-Regis, Authorized Officer, on Feb. 28, 2007, in PCT/US2005/05579, the PCT counterpart to the present application.

Written Opinion of the International Searching Authority, PCT—ISA/US, WO 2007/079103, PCT counterpart of the present application, Lee W. Young, Authorized Officer, Jun. 25, 2007.

International Preliminary Report on Patentability, International Bureau of WIPO, Geneva CH by Agnes Wittmann-Regis, Authorized Officer, on Feb. 28, 2007 in PCT/US2005/05579, the PCT counterpart to the present application.

Supplementary European Search Report, European Patent Office, Munich DE, WO 2007/079103, PCT counterpart of the present application, Jun. 29, 2009.

(56) References Cited

OTHER PUBLICATIONS

Non-Final Office Action mailed May 19, 2006, in U.S. Appl. No. 10/782,357.
Non-Final Office Action mailed Nov. 22, 2006, in U.S. Appl. No. 10/782,357.
Non-Final Office Action mailed May 29, 2007, in U.S. Application No. 10/782,357.
Non-Final Office Action mailed Nov. 30, 2007, in U.S. Appl. No. 10/782,357.
Non-Final Office Action mailed Jun. 5, 2008, in U.S. Appl. No. 10/782,357.
Non-Final Office Action mailed Jan. 9, 2009, in U.S. Appl. No. 10/782,357.
Final Office Action mailed Aug. 7, 2009, in U.S. Appl. No. 10/782,357.
Non-Final Office Action mailed Mar. 31, 2010, in U.S. Appl. No. 10/782,357.
Final Office Action mailed Dec. 6, 2010, in U.S. Appl. No. 10/782,357.
Notice of Allowance mailed Apr. 18, 2011, in U.S. Appl. No. 10/782,357.
Non-Final Office Action mailed Mar. 24, 2006, in U.S. Appl. No. 10/783,304.
Non-Final Office Action mailed Dec. 6, 2006, in U.S. Appl. No. 10/783,304.
Final Office Action mailed Jun. 12, 2007, in U.S. Appl. No. 10/783,304.
Notice of Allowance mailed Dec. 13, 2007, in U.S. Appl. No. 10/783,304.
Non-Final Office Action mailed Aug. 19, 2009, in U.S. Appl. No. 11/966,123.
Final Office Action mailed May 28, 2010, in U.S. Appl. No. 11/966,123.
Notice of Allowance mailed Jan. 13, 2010, in U.S. Appl. No. 11/317,529.
Non-Final Office Action mailed May 26, 2009, in U.S. Appl. No. 11/317,529.
Notice of Allowance mailed Jul. 27, 2010, in U.S. Appl. No. 11/643,293.
Non-Final Office Action mailed Nov. 4, 2009, in U.S. Appl. No. 11/643,293.
Final Office Action mailed Jul. 11, 2011, U.S. Appl. No. 11/644,064.
Non-Final Office Action mailed Oct. 27, 2010, U.S. Appl. No. 11/644,064.
I. H. Campbell et al., Excitation Transfer Processes in a Phosphor-Doped Poly(P-Phenylene Vinylene) Light-Emitting Diode, Physical Review B, vol. 65:085210-1-085210-8, 2002.
D. F. O'Brien et al., Electrophorescence From a Doped Polymer Light Emitting Diode, Synthetic Metals, vol. 116:379-383, 2001.
Takakazu Yamamoto, Electrically Conducting and Thermally Stable n-Conjugated Poly (Arylene)S Prepared by Organometallic Processes, Prog. Polym. Sci., vol. 17:1153-1205, 1992.
I. Colon et al., High Molecular Weight Aromatic Polymers by Nickel Coupling of Aryl Polychlorides, Journal of Polymer Science: Part A:Polymer Chemistry, vol. 28:367-383, 1990.
Braig, Thomas et al., Crosslinkable hole-transporting polymers by palladium-catalyzed C-N-coupling reaction, Macromol. Rapid Commun., 2000, 583-589, 21(9), Wiley-VCH Verlag GmbH, Weinheim.
Sadighi, Joseph P. et al., Palladium-Catalyzed Synthesis of Monodisperse, Controlled-Length, and Functionalized Oligoanilines.
Nuyken, Oskar et al., Crosslinkable hole- and electron-transport materials for application in organic light emitting devices (OLEDs), Designed Monomers and Polymers, 2002, 195-210, 5(2,3).
Thelakkat, M. et al., Synthesis and Properties of Novel Hole Transport Materials for Electroluminescent Devices in Macromolecular Symposia, vol. 125, 1997, pp. 157-184, Wiley VCH, Weinheim, Germany.

International Search Report and Written Opinion of the International Searching Authority Dated Jun. 30, 2005 PCT/US2005/005584, Dated Feb. 17, 2005.
Bacher, Andreas et al., Photo-Corss-Linked Triphenylenes as Novel Insoluble Hole Transport Materials in Organic LEDs, Macromolecules, 1999, 4551-4557, 32, American Chemical Society.
Schmitz et al. Advanced Materials 1999, 11, No. 10 p. 821-826.
Bedford et al., "Hydroxyamine O-benzyl Ether as an Ammonia Equivalent in the Catalytic Amination of Aryl Halides," Tetrahedron Letters, 2007, vol. 48(51), pp. 8947-8950.
Byung Doo Chin et al: "Improved blue light-emitting polymeric device by the tuning of drift mobility and charge balance" Applied Physics Letters, vol. 84, No. 10, 2004, pp. 1777-1779, XP002608479.
Chen et al—Efficient, Blue Light-Emitting Diodes Using Cross-Linked Layers of Polymeric Arylamine and Fluorene, Synthetic Metals 107, 1999, pp. 129-135.
Database Chemical Abstracts—Noguchi, Takanobu et al. Process for Production of High-Molecular Compounds Useful for Polymer LED or the Like. XP002635436.
Desmarets et al; "Nickel-Catalyzed sequential amination of aryl- and heteroaryl di- and trichlorides," Tetrahedron, vol. 57, 2001, pp. 7657-7664.
Hartwig, "Palladium-Catalyzed Amination of Aryl Halides and Sulfonates," Modern Arene Chemistry, 2002, pp. 107-168; Astruc, D., Editor; Wiley-VCH Verlag GmbH & Co. KGaA, Weinheim, Germany.
He et al—High-Efficiency Organic Polymer Light-Emitting Heterostructure Devices on Flexible Plastic Substates, 2000, Applied Physics Letters, vol. 76, No. 6, pp. 661-663.
He et al., "High-efficiency Organic Polymer Light-emitting Heterostructure Devices on Flexible Plastic Substrates," Feb. 2000; American Institute of Physics, Chem Abstract 132: 229208.
Hino et al., "Efficient Low-Molecule Phosphorescent Organic Light-Emitting Diodes Fabricated by Wet-Processing," Organic Electronics, vol. 5, No. 5, Sep. 2004, pp. 265-270.
Itano et al., "Fabrication and Performances of a Double-Layer Organic Electroluminescent Device Using a Novel Starburst Molecule, 1,3,5-Tris[N-(4-diphenylaminophenyl)phenylamino]benzene, as a Hole-Transport Material and Tris (8-quinolinolato)aluminum as an Emitting Material," IEEE Transactions on Electron Devices, vol. 44, No. 8, Aug. 1, 1997, pp. 1218-1221.
Thaimattam et al., "Inclusion Compounds of Tetrakis(4-nitrophenyl)methane: C—H—O Networks, Pseudomorphism, and Structural Transformations," Journal of the American Chemical Society, 2001, vol. 123(19), pp. 4432-4445.
Klapars et al., "A General and Efficient Copper Catalyst for the Amidation of Aryl Halides and the N-Arylation of Nitrogen Heterocycles," Journal of the American Chemical Society, 2001, vol. 123, pp. 7727-7729.
Nakatsuka et al., "Organic Field-effect Electroluminescent Devices with Long Lifetime," 1999, Mitsui Chemicals Inc., Japan, Chem Abstract 131: 191677.
Nakatsuka et al., "Preparation of 2,7-bis[(bisdiarylamino)aryl] fluorine Derivatives as Hole-transport Materials for Organic Electroluminescent Devices," 2001, Mitsui Chemicals Inc., Japan, Chem Abstract 134: 172027.
Pan et al., "Theoretical Investigations of the Molecular Conformation and Reorganization of Energies in the Organic Diamines as Hole-transporting Materials," Journal of Physical Organic Chemistry, 2007, vol. 20(10), pp. 743-753.
Qiang Fang et al—New Alternative Copolymer Constituted of Fluorene and Triphenylamine Units With a Tunable—CHO Group in the Side Chain, Macromolecules, vol. 37, 2004, pp. 5894-5899.
Wang et al., "Electronic Structure and Molecular Orbital Study of Hole-transport Material Triphenylamine Derivatives," Journal of Luminescence, 2007, vol. 124(2), pp. 333-342.
Wolfe et al., "Nickel-Catalyzed Amination of Aryl Chlorides," Journal of the American Chemical Society, 1997, vol. 119, pp. 6054-6058.

(56) References Cited

OTHER PUBLICATIONS

Wolfe et al., "Simple, Efficient Catalyst Systems for the Palladium-Catalyzed Amination of Aryl Chlorides, Bromides, and Triflates," Organic Chemistry, 2000, vol. 65, pp. 1158-1174.

Zhu et al., "Effect of ITO Carrier Concentration on the Performance of Light-Emitting Diodes," 2000; Material Research Society; Chem Abstract 134: 122994.

Extended European Search Report for Application No. 11008574.3; Dec. 23, 2011.

Extended European Search Report for Application No. 11008575.0; Feb. 16, 2012.

International Search Report for Application No. PCT/US2005/005579, counterpart to U.S. Appl. No. 10/782,357 (US 7960587); M. Kovecs, Authorized Officer; Jun. 3, 2005.

International Search Report for Application No. PCT/US2010/053124, published as WO 2011/049904; counterpart to U.S. Appl. No. 12/907,067; KIPO; Kang Young Kim, Authorized Officer; Jul. 25, 2011.

International Search Report for Application No. PCT/US2010/053209, published as WO 2011/049953; counterpart to U.S. Appl. No. 12/907,058; KIPO; Kang Young Kim, Authorized Officer; Jul. 25, 2011.

International Search Report, Korean Intellectual Property Office, Daejeon, Republie of Korea, PCT/US2009/068921, PCT Counterpart of the Present U.S. Appl. No. 12/643,486, Hyun Shik Oh, Authorized Officer, Aug. 5, 2010.

Office Action for Application No. EP 06848202.5; EPO; Dec. 30, 2011.

PCT International Search Report for International Application No. PCT/US2006/49339, Lee W. Young Authorized Officer, Sep. 24, 2007.

Non-Final Office Action for U.S. Appl. No. 12/643,486, counterpart to U.S. Appl. No. 12/907,067, Jul. 18, 2012.

\* cited by examiner

TRIARYLAMINE COMPOUNDS FOR USE IN ORGANIC LIGHT-EMITTING DIODES

RELATED APPLICATION DATA

This application claims priority under 35 U.S.C. §119(e) from U.S. Provisional Application Nos. 61/252,808 filed on Oct. 19, 2009 and 61/362,427 filed on Jul. 8, 2010, which is incorporated by reference herein in its entirety.

BACKGROUND

1. Field of the Disclosure

This invention relates to triarylamine compounds. It also relates to electronic devices in which at least one active layer includes such a compound.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Organometallic compounds such as cyclometallated complexes of Ir and Pt are known to show electroluminescence. Semiconductive conjugated polymers have also been used as electroluminescent components. In many cases the electroluminescent compound is present as a dopant in a host material.

There is a continuing need for new materials for electronic devices.

SUMMARY

There is provided an electronic device comprising an active layer comprising a compound having Formula I, II, or III:

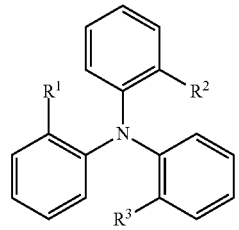

Formula I

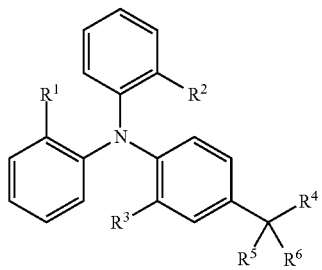

Formula II

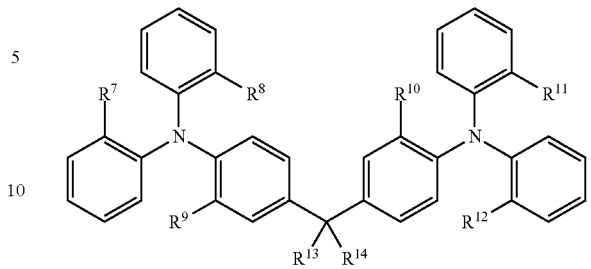

Formula III where:
R¹, R², and R³ are the same or different and are alkyl groups, where two or more of the alkyl groups may be joined together to form a cyclic or multicyclic group;
R⁴, R⁵, and R⁶ are the same or different and are selected from the group consisting of alkyl groups and aryl groups, where R⁵ and R⁶ may be joined together to form a cyclic group;
R⁷ and R⁸ are the same or different and are alkyl groups
R⁹ is selected from the group consisting of H, D, and alkyl groups, where two or more of R⁷, R⁸ and R⁹ may be joined together to form a cyclic or multicyclic group;
R¹⁰ and R¹¹ are the same or different and are alkyl groups
R¹² is selected from the group consisting of H, D, and alkyl groups, where two or more of R¹⁰, R¹¹ and R¹² may be joined together to form a cyclic or multicyclic group; and
R¹³ and R¹⁴ are the same or different and are selected from the group consisting of alkyl groups, aryl groups, and arylamino groups, or R¹³ and R¹⁴ may be joined together to form a cyclic group.

There is further provided an electroactive composition comprising (a) a triarylamine having Formula I, II, or III, and (b) an organometallic dopant capable of electroluminescence having an emission maximum between 380 and 750 nm.

There is further provided an organic electronic device comprising a first electrical contact layer, a second electrical contact layer, and at least one active layer therebetween, wherein the active layer comprises a triarylamine compound having Formula I, Formula II, or Formula III.

BRIEF DESCRIPTION OF THE DRAWINGS

Embodiments are illustrated in the accompanying figures to improve understanding of concepts as presented herein.

Figure 1:
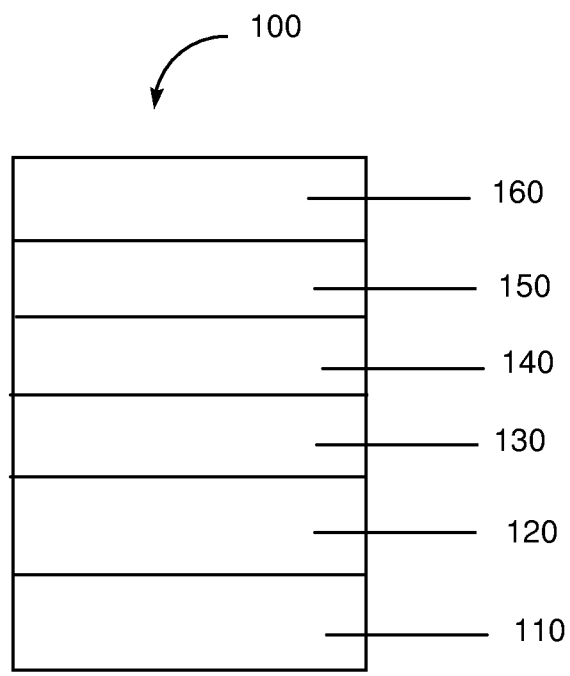
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments are disclosed herein and are exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Triarylamine Compound, the Electronic Device, and finally Examples.

1. Definitions and Clarification of Terms

Before addressing details of embodiments described below, some terms are defined or clarified.

As used herein, the term "aliphatic ring" is intended to mean a cyclic group that does not have delocalized pi electrons. In some embodiments, the aliphatic ring has no unsaturation. In some embodiments, the ring has one double or triple bond.

The term "alkyl" is intended to mean a group derived from an aliphatic hydrocarbon having one point of attachment, and includes a linear, a branched, or a cyclic group. The term is intended to include heteroalkyls. The term "hydrocarbon alkyl" refers to an alkyl group having no heteroatoms. The term "deuterated alkyl" is an alkyl having at least one available H replaced by D. In some embodiments, an alkyl group has from 1-20 carbon atoms.

The term "branched alkyl" refers to an alkyl group having at least one secondary or tertiary carbon. The term "secondary alkyl" refers to a branched alkyl group having a secondary carbon atom. The term "tertiary alkyl" refers to a branched alkyl group having a tertiary carbon atom. In some embodiments, the branched alkyl group is attached via a secondary or tertiary carbon.

The term "aryl" is intended to mean a group derived from an aromatic hydrocarbon having one point of attachment. The term "aromatic compound" is intended to mean an organic compound comprising at least one unsaturated cyclic group having delocalized pi electrons. The term is intended include heteroaryls. The term "hydrocarbon aryl" is intended to mean aromatic compounds having no heteroatoms in the ring. The term aryl includes groups which have a single ring and those which have multiple rings which can be joined by a single bond or fused together. The term "deuterated aryl" refers to an aryl group having at least one available H bonded directly to the aryl replaced by D. The term "arylene" is intended to mean a group derived from an aromatic hydrocarbon having two points of attachment. In some embodiments, an aryl group has from 3-60 carbon atoms.

The term "charge transport," when referring to a layer, material, member, or structure is intended to mean such layer, material, member, or structure facilitates migration of such charge through the thickness of such layer, material, member, or structure with relative efficiency and small loss of charge. Hole transport layers, materials, members and structure facilitate positive charge. Electron transport layers, materials, members and structure facilitate negative charge. Although light-emitting materials may also have some charge transport properties, the terms "charge, hole or electron transport layer, material, member, or structure" are not intended to include a layer, material, member, or structure whose primary function is light emission.

The term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

The term "deuterated" is intended to mean that at least one H has is been replaced by D. The deuterium is present in at least 100 times the natural abundance level. A "deuterated derivative" of compound X has the same structure as compound X, but with at least one D replacing an H.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" when referring to a layer or material, is intended to mean a layer or material that exhibits electronic or electro-radiative properties. In an electronic device, an electroactive material electronically facilitates the operation of the device. Examples of electroactive materials include, but are not limited to, materials which conduct, inject, transport, or block a charge, where the charge can be either an electron or a hole, and materials which emit radiation or exhibit a change in concentration of electron-hole pairs when receiving radiation. Examples of inactive materials include, but are not limited to, planarization materials, insulating materials, and environmental barrier materials.

The prefix "hetero" indicates that one or more carbon atoms have been replaced with a different atom. In some embodiments, the different atom is N, O, or S.

The term "host material" is intended to mean a material to which a dopant is added. The host material may or may not have electronic characteristic(s) or the ability to emit, receive, or filter radiation. In some embodiments, the host material is present in higher concentration.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

All groups can be substituted or unsubstituted unless otherwise indicated. In some embodiments, the substituents are selected from the group consisting of D, halide, alkyl, alkoxy, aryl, aryloxy, cyano, and $NR_2$, where R is alkyl or aryl.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, $81^{st}$ Edition, 2000).

2. Triarylamine Compound

The triarylamine compound has Formula I, II, or III:

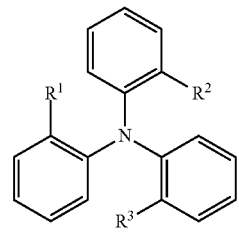

Formula I

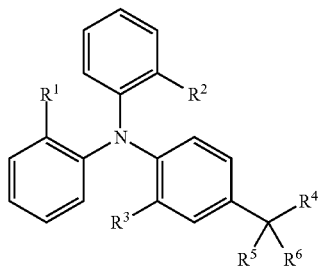

Formula II

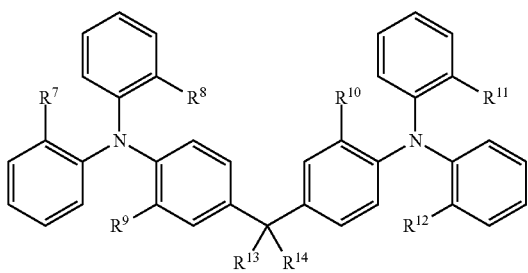

Formula III where:
- R¹, R², and R³ are the same or different and are alkyl groups, where two or more of the alkyl groups may be joined together to form a cyclic or multicyclic group;
- R⁴, R⁵, and R⁶ are the same or different and are selected from the group consisting of alkyl groups and aryl groups, where R⁵ and R⁶ may be joined together to form a cyclic group;
- R⁷ and R⁸ are the same or different and are alkyl groups
- R⁹ is selected from the group consisting of H, D, and alkyl groups, where two or more of R⁷, R⁸ and R⁹ may be joined together to form a cyclic or multicyclic group;
- R¹⁰ and R¹¹ are the same or different and are alkyl groups
- R¹² is selected from the group consisting of H, D, and alkyl groups, where two or more of R¹⁰, R¹¹ and R¹² may be joined together to form a cyclic or multicyclic group; and
- R¹³ and R¹⁴ are the same or different and are selected from the group consisting of alkyl groups, aryl groups, and arylamino groups, or R¹³ and R¹⁴ may be joined together to form a cyclic group.

In some embodiments, the alkyl group has 1-3 carbon atoms. In some embodiments, the alkyl group is methyl. In some embodiments, the alkyl group is deuterated.

In some embodiments, the aryl group is selected from the group consisting of phenyl, biphenyl, naphthyl, deuterated derivatives thereof, and a group having Formula IV:

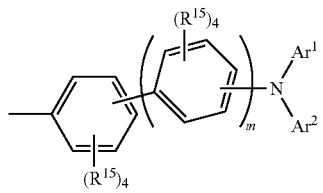

Formula IV where:
- Ar¹ and Ar² are the same or different and are aryl groups, or Ar¹ and Ar² can be joined together to form a carbazole group;
- R¹⁵ is the same or different at each occurrence and is selected from is the group consisting of H, D, and alkyl, or adjacent R¹⁵ groups may be joined together to form an aromatic ring; and
- m is the same or different at each occurrence and is an integer from 0 to 5.

In some embodiments, the triarylamine compound is at least 10% deuterated. By this is meant that at least 10% of the hydrogens in the compound have been replaced by deuterium. In some embodiments, the triarylamine compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated;

Some examples of triarylamine compounds having the above formulae include, but are not limited to, the compounds shown below.

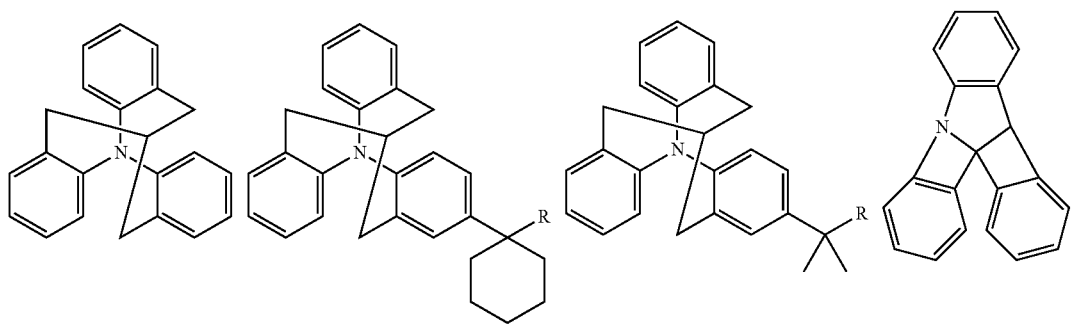

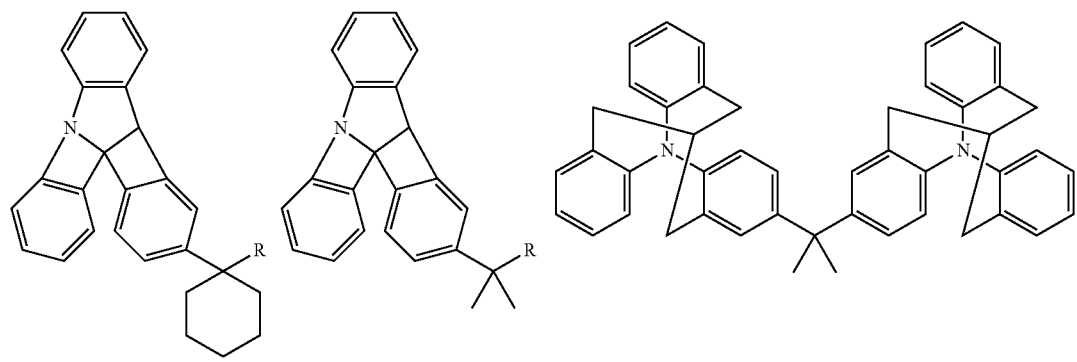
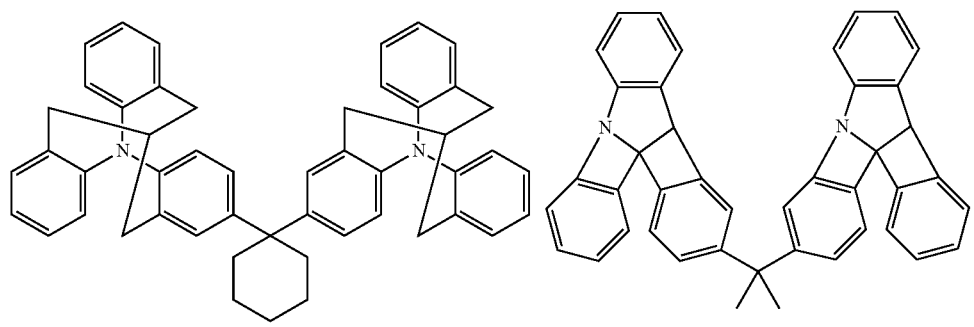
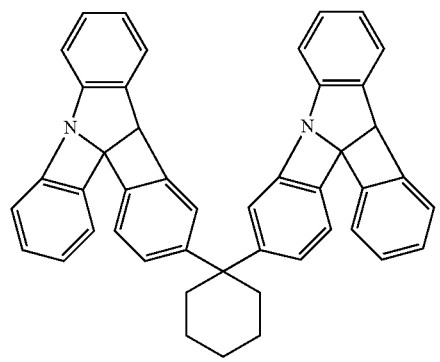
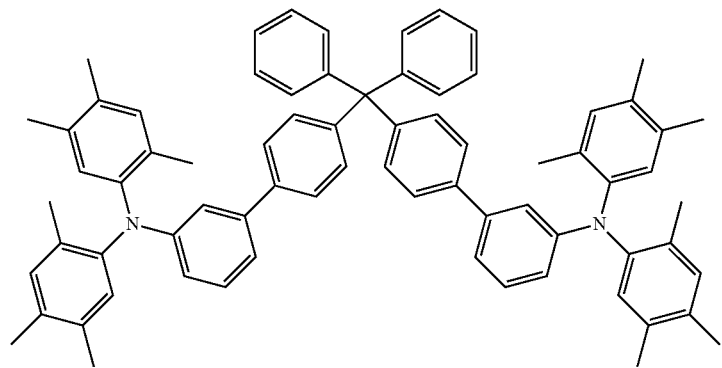

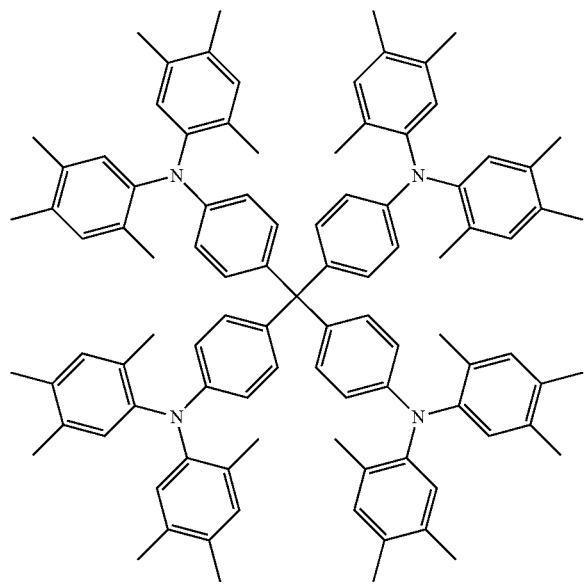
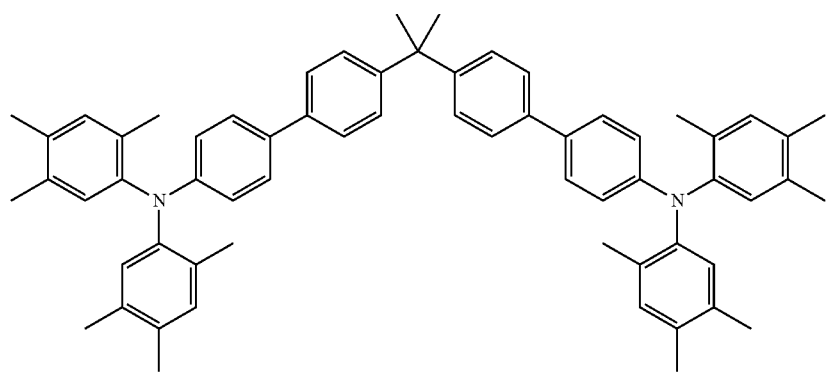
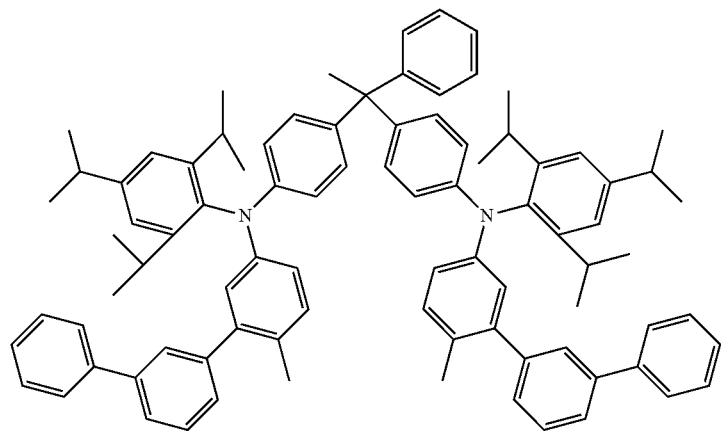

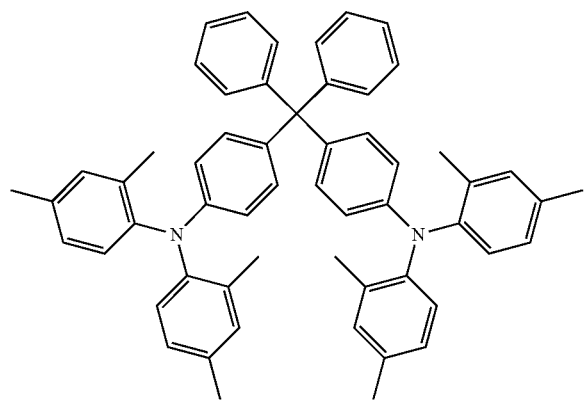
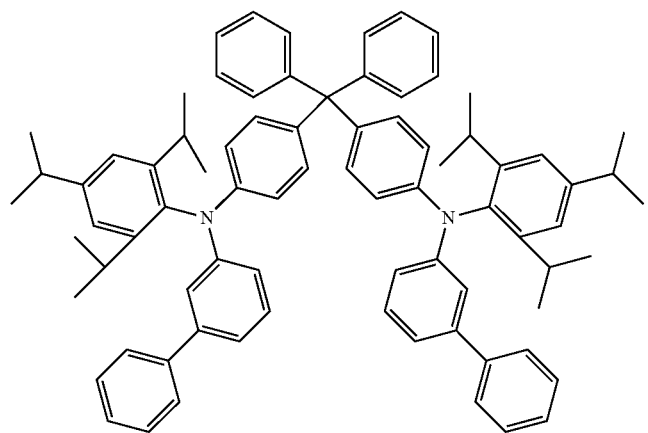
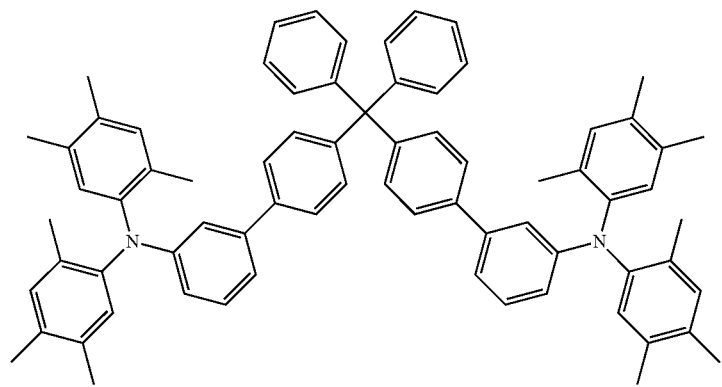

-continued
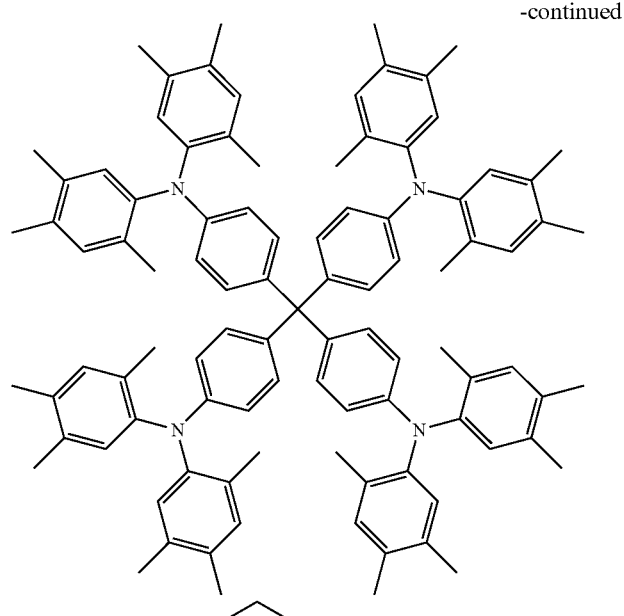
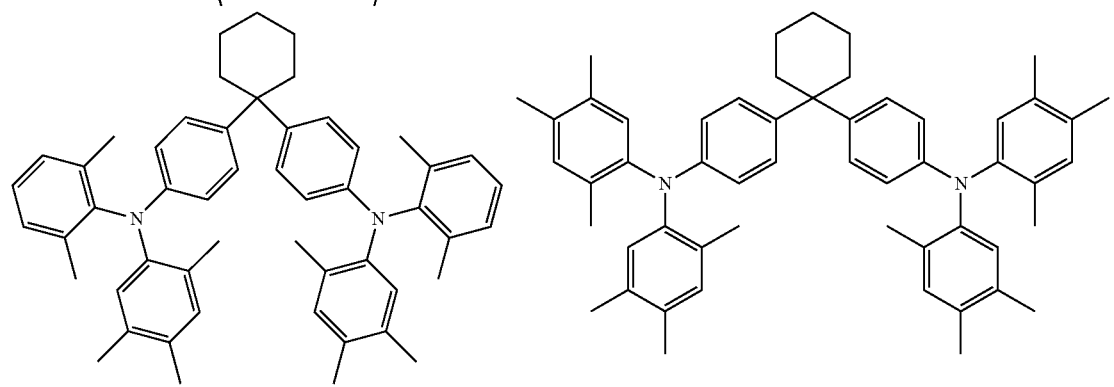
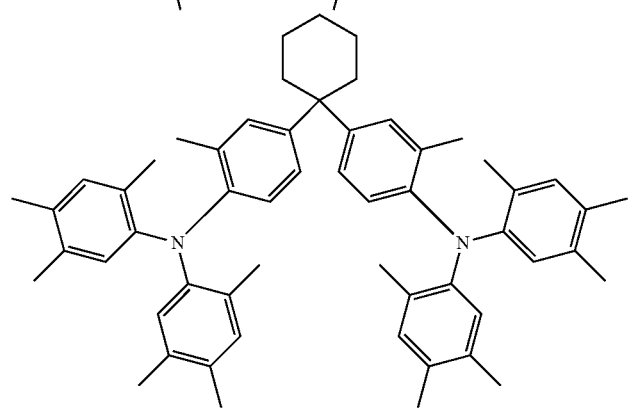
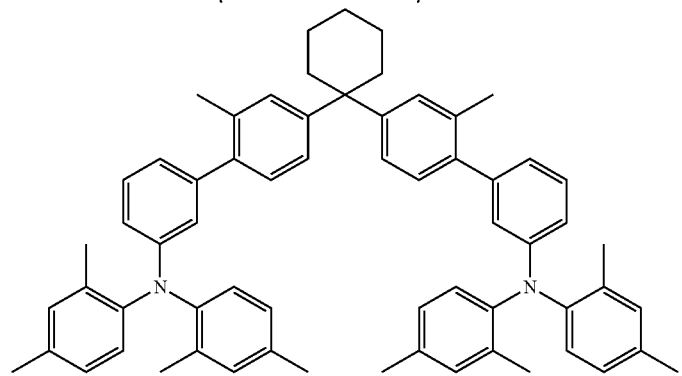

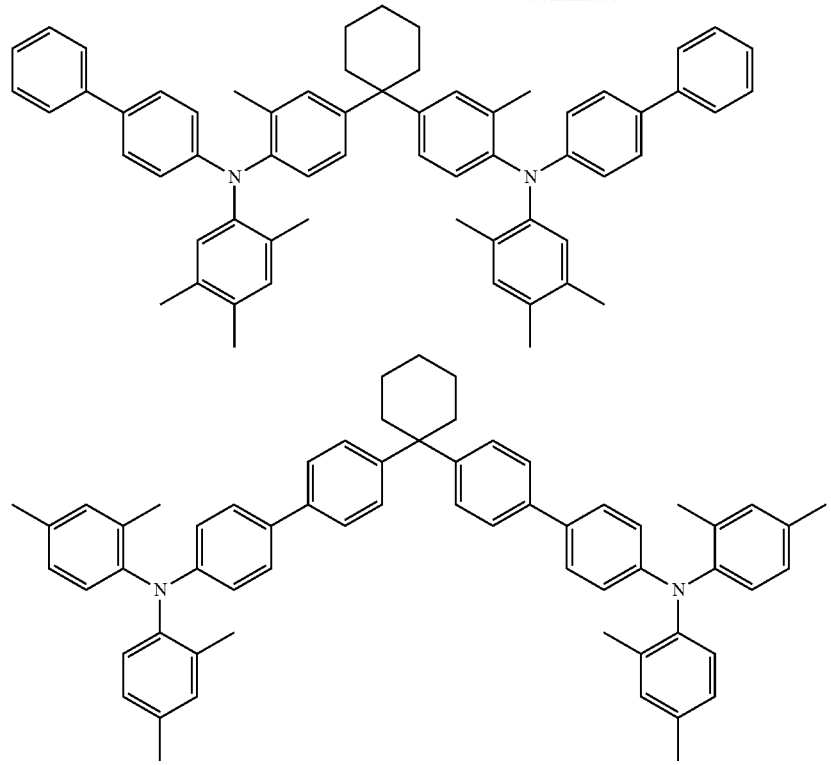

-continued

The new triarylamine compounds can be prepared by known coupling and substitution reactions. The deuterated analog compounds can then be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, etc. Exemplary preparations are given in the Examples.

3. Electronic Device

Organic electronic devices that may benefit from having one or more layers comprising the triarylamine compounds described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors, or biosensors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and an electroactive layer 140 between them. Adjacent to the anode may be a hole injection layer 120. Adjacent to the hole injection layer may be a hole transport layer 130, comprising hole transport material. Adjacent to the cathode may be an electron transport layer 150, comprising an electron transport material. Devices may use one or more additional hole injection or hole transport layers (not shown) next to the anode 110 and/or one or more additional electron injection or electron transport layers (not shown) next to the cathode 160. In some embodiments, the devices have additional layers to aid in processing or to improve functionality.

Layers 120 through 150 are individually and collectively referred to as the active layers.

Figure 2:
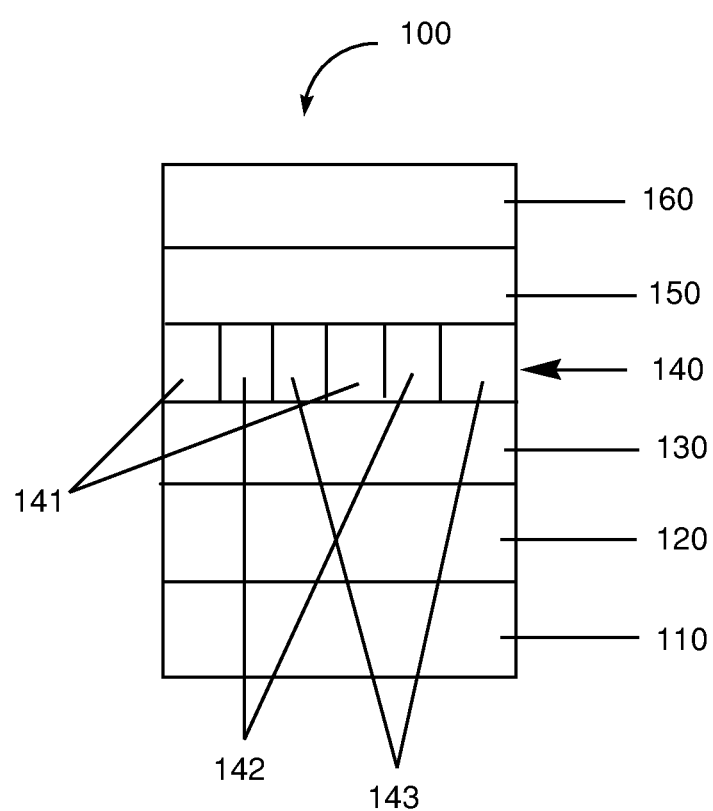
FIG. 2 includes a schematic diagram of another example of an organic electronic device.

In some embodiments, the electroactive layer 140 is pixelated, as shown in FIG. 2. Layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In one embodiment, the different layers have the following range of thicknesses: anode 110, 500-5000 Å, in one embodiment 1000-2000 Å; hole injection layer 120, 50-2000 Å, in one embodiment 200-1000 Å; hole transport layer 130, 50-2000 Å, in one embodiment 200-1000 Å; electroactive layer 140, 10-2000 Å, in one embodiment 100-1000 Å; layer 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 100, the electroactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966).

The triarylamine compounds described herein have particular utility in organic light-emitting diodes ("OLEDs"). In OLEDs, the light-emitting material is frequently an organometallic compound containing a heavy atom such as Ir, Pt, Os, Rh, and the like. The lowest excited state of these organometallic compounds often possesses mixed singlet and triplet character (Yersin, Hartmut; Finkenzeller, Walter J., Triplet emitters for organic light-emitting diodes: basic properties. Highly Efficient OLEDs with Phosphorescent Materials (2008)). Because of the triplet character, the excited state can transfer its energy to the triplet state of a nearby molecule, which may be in the same or an adjacent layer. This results in luminescence quenching. To prevent such luminescence quenching in an OLED device, the triplet state energy of the material used in various layers of the OLED device has to be comparable or higher than the lowest excited state energy of the organometallic emitter. For example, it has been demonstrated that for the green emitter Ir(ppy)$_3$, the use of NPB as the hole transport layer resulted in luminance quenching due to the low triplet state energy of NPB (Y. Wang, Appl. Phys. Lett., 85, 4848 (2004)). It should be noted that the excited state energy of an organometallic emitter can be determined from the 0-0 transition in the luminance spectrum, which is typically at higher energy than the luminance peak.

If the recombination zone in the emissive layer of the OLED device is located on the hole transport side, then the exciton luminance is more sensitive to the triplet energy of the hole transport layer used. Conversely, if the recombination zone is located on the electron transport side, the exciton luminance is more sensitive to the triplet energy of the electron transport layer used. The exciton luminance tends to be most sensitive to the triplet energy of the host material.

One commonly used hole transport material with high triplet energy is 1,1-bis[(di-4-tolylamino)phenyl]cyclohexane ("TAPC"). There is a continuing need to further increase its triplet energy to be used for green, blue-green, and blue emitters with triplet character. The new triarylamine compounds having Formula I, II or III have increased triplet energy due to the twisting of the aryl-N groups out of plane. Thus the new triarylamine compounds are particularly useful in devices with organometallic emitters. The triarylamine compounds may be present as the hole transport material in layer 130, as the host material in layer 140, or both.

The organic electronic device comprises a first electrical contact layer, a second electrical contact layer, and at least one active layer therebetween, wherein the active layer comprises a triarylamine compound having Formula I, Formula II, or Formula III. In some embodiments, the active layer is the hole transport layer 130. In some embodiments, the active layer is the electroactive layer 140.

In some embodiments, an organic electron device comprises an anode, a first electroactive layer, a second electroactive layer, and a cathode, wherein the first electroactive layer comprises a compound having Formula I, II, or III, and the second electroactive layer comprises an organometallic compound capable of electroluminescence having an emission maximum between 380 and 750 nm. In some embodiments, the first electroactive layer is a hole transport layer and the second electroactive layer is an electroluminescent layer. In some embodiments, the second electroactive layer comprises a compound having Formula I, II, or III.

a. Hole Transport Layer

In some embodiments, the hole transport layer comprises the new triarylamine compound having Formula I, II or III. In some embodiments, the hole transport layer consists essentially of the new triarylamine compound. The triarylamine compound layer may be formed by any deposition method, including vapor deposition, liquid deposition, and thermal transfer.

In some embodiments, the hole transport layer comprises a different hole transport material. Examples of other hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis (naphthalen-1-yl)-N,N'-bis-(phenyl)benzidine (□-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

b. Electroactive Layer

In some embodiments, the new triarylamine compound having Formula I, II, or III is a host for an electroluminescent material in electroactive layer 140. In some embodiments, the electroactive composition comprises (a) a triarylamine compound host having Formula I, II, or III, and (b) an organometallic dopant capable of electroluminescence having an emission maximum between 380 and 750 nm. In some embodiments, the electroactive composition further comprises (c) a second host material. In some embodiments, the electroactive composition consists essentially of (a) a triarylamine compound host having Formula I, II, or III, and (b) an organometallic dopant capable of electroluminescence having an emission maximum between 380 and 750 nm. In some embodiments, the electroactive composition consist essentially of (a) a triarylamine compound host having Formula I, II, or III, and (b) an organometallic dopant capable of electroluminescence having an emission maximum between 380 and 750 nm, and (c) a second host material.

The new triarylamine compounds can be used as a host for dopants with any color of emission. In some embodiments, the new triarylamine compounds are used as hosts for electroluminescent materials having an emission color ranging from green to blue.

Examples of other host materials include, but are not limited to, chrysenes, phenanthrenes, triphenylenes, phenanthrolines, naphthalenes, anthracenes, quinolines, isoquinolines, quinoxalines, phenylpyridines, benzodifurans, indolocarbazoles, and metal quinolinate complexes.

The amount of dopant present in the electroactive composition is generally in the range of 3-20% by weight, based on the total weight of the composition; in some embodiments, 5-15% by weight. When a second host is present, the ratio of triarylamine host having Formula I, II, or III to second host is generally in the range of 1:20 to 20:1; in some embodiments, 5:15 to 15:5. In some embodiments, the triarylamine host material is at least 50% by weight of the total host material; in some embodiments, at least 70% by weight.

In some embodiments, the second host material has Formula V:

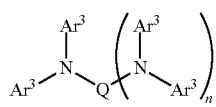

Formula V where:
Ar$^a$ is the same or different at each occurrence and is an aryl group;
Q is selected from the group consisting of multivalent aryl groups and

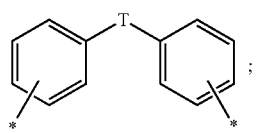

T is selected from the group consisting of $(CR')_a$, $SiR_2$, S, $SO_2$, PR, PO, $PO_2$, BR, and R;
R is the same or different at each occurrence and is selected from the group consisting of alkyl, and aryl;
R' is the same or different at each occurrence and is selected from the group consisting of H and alkyl;
a is an integer from 1-6; and
n is an integer from 0-6.
While n can have a value from 0-6, it will be understood that for some Q groups the value of n is restricted by the chemistry of the group. In some embodiments, n is 0 or 1.

In some embodiments of Formula IV, adjacent Ar groups are joined together to form rings such as carbazole. In Formula IV, "adjacent" means that the Ar groups are bonded to the same N.

In some embodiments, Ar$^3$ is independently selected from the group consisting of phenyl, biphenyl, terphenyl, quaterphenyl, naphthyl, phenanthryl, naphthylphenyl, and phenanthrylphenyl. Analogs higher than quaterphenyl, having 5-10 phenyl rings, can also be used.

In some embodiments, at least one of Ar$^3$ has at least one substituent. Substituent groups can be present in order to alter the physical or electronic properties of the host material. In some embodiments, the substituents improve the processability of the host material. In some embodiments, the substituents increase the solubility and/or increase the Tg of the host material. In some embodiments, the substituents are selected from the group consisting of D, alkyl groups, alkoxy groups, silyl groups, siloxane, and combinations thereof.

In some embodiments, Q is an aryl group having at least two fused rings. In some embodiments, Q has 3-5 fused aromatic rings. In some embodiments, Q is selected from the group consisting of chrysene, phenanthrene, triphenylene, phenanthroline, naphthalene, anthracene, quinoline and isoquinoline.

The dopant is an electroactive material which is capable of electroluminescence having an emission maximum between 380 and 750 nm. In some embodiments, the dopant emits red, green, or blue light. Examples of red light-emitting materials include, but are not limited to, cyclometalated complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

Examples of green light-emitting materials include, but are not limited to, cyclometalated complexes of Ir having phenylpyridine ligands, diaminoanthracenes, and polyphenylenevinylene polymers. Green light-emitting materials have been disclosed in, for example, published PCT application WO 2007/021117.

Examples of blue light-emitting materials include, but are not limited to, diarylanthracenes, diaminochrysenes, diaminopyrenes, cyclometalated complexes of Ir having phenylpyridine ligands, and polyfluorene polymers. Blue light-emitting materials have been disclosed in, for example, U.S. Pat. No. 6,875,524, and published US applications 2007-0292713 and 2007-0063638.

In some embodiments, the dopant is an organometallic complex. In some embodiments, the dopant is a cyclometalated complex of iridium or platinum. Such materials have been disclosed in, for example, U.S. Pat. No. 6,670,645 and Published PCT Applications WO 03/063555, WO 2004/016710, and WO 03/040257.

In some embodiments, the dopant is a complex having the formula $Ir(L1)_x(L2)_y(L3)_z$; where
L1 is a monoanionic bidentate cyclometalating ligand coordinated through carbon and nitrogen;
L2 is a monoanionic bidentate ligand which is not coordinated through a carbon;
L3 is a monodentate ligand;
x is 1-3;
y and z are independently 0-2;
and x, y, and z are selected such that the iridium is hexacoordinate and the complex is electrically neutral.
Some examples of formulae include, but are not limited to, $Ir(L1)_3$; $Ir(L1)_2(L2)$; and $Ir(L1)_2(L3)(L3')$, where L3 is anionic and L3' is nonionic.

In some embodiments, L1 has a structure in which a N-heterocyclic ring is bonded to a second aromatic ring, as shown schematically below.

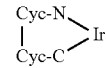

Examples of N-heterocyclic rings include, but are not limited to, pyridine, quinoline, isoquinoline, diazines, pyrazoles, and triazines. Examples of the second aromatic ring include, but are not limited to, phenyl, pyrrole, thiophene, and pyridine. The N-heterocyclic and second aromatic rings may have one or more substituents selected from the group consisting of D, halide (especially F), alkyl, alkoxy, aryl aryloxy, silyl, arylamino, and cyano.

Examples of L1 ligands include, but are not limited to phenylpyridines, phenylquinolines, phenylpyrimidines, phenylpyrazoles, thienylpyridines, thienylquinolines, thienylpyrimidines, and 1,7-phenanthroline. As used herein, the term "quinolines" includes "isoquinolines" unless otherwise specified. These ligands may have substituents as discussed above.

Monoanionic bidentate ligands, L2, are well known in the art of metal coordination chemistry. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanols (phosphinoalkoxide ligands).

In some embodiments, L2 is selected from the group consisting of

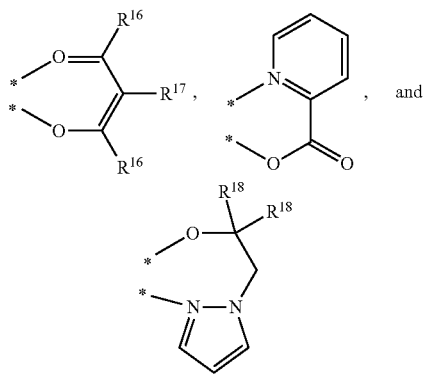

where:
$R^{16}$ is the same or different at each occurrence and is selected from the group consisting of alkyl and fluoroalkyl;
$R^{17}$ is H, D or F;
$R^{18}$ is the same or different at each occurrence and is selected from the group consisting of alkyl and fluoroalkyl; and
* represents a point of coordination with Ir.

Monodentate ligand L3 can be anionic or nonionic. Anionic ligands include, but are not limited to, H⁻ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L2, such as β-enolates and phosphinoakoxides, can act as monodentate ligands. The monodentate ligand can also be a coordinating anion such as halide, cyanide, isocyanide, nitrate, sulfate, hexahaloantimonate, and the like. These ligands are generally available commercially.

The monodentate L3 ligand can also be a non-ionic ligand, such as CO or a monodentate phosphine ligand.

In some embodiments, one or more of the ligands has at least one substituent selected from the group consisting of F and fluorinated alkyls.

The iridium complex dopants can be made using standard synthetic techniques as described in, for example, U.S. Pat. No. 6,670,645.

Some non-limiting examples of iridium complex dopants having red or red-orange emission are given below.

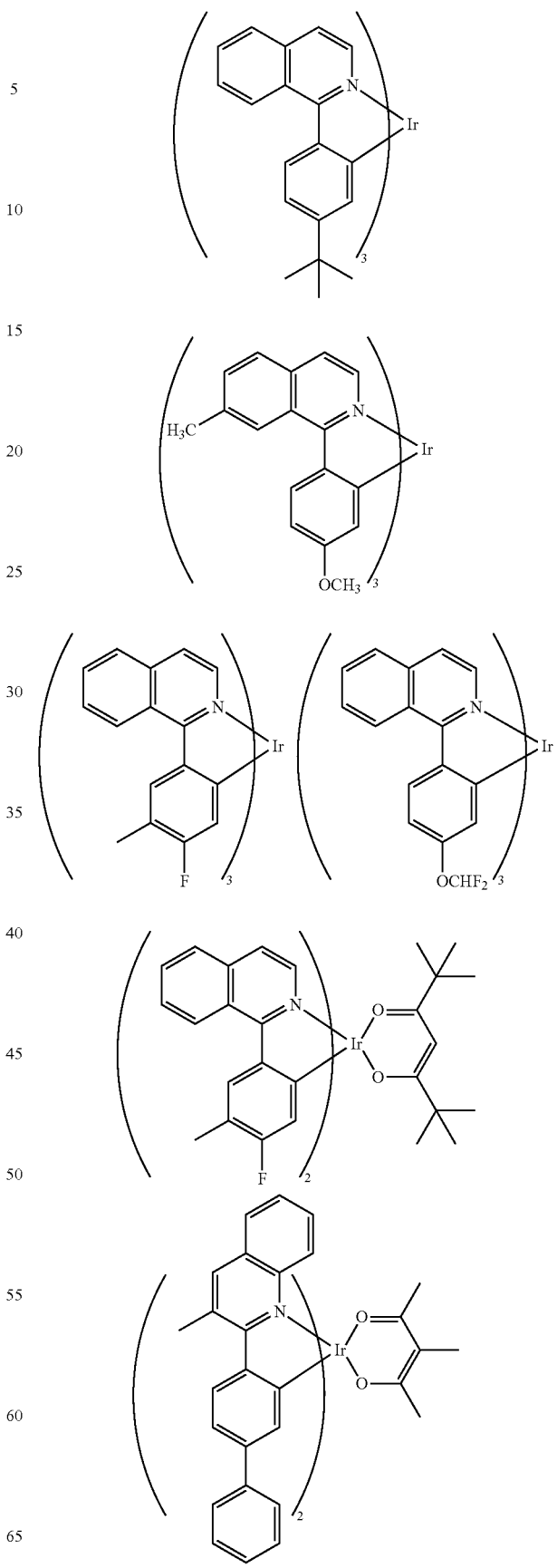

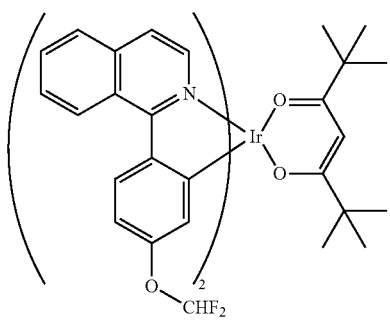
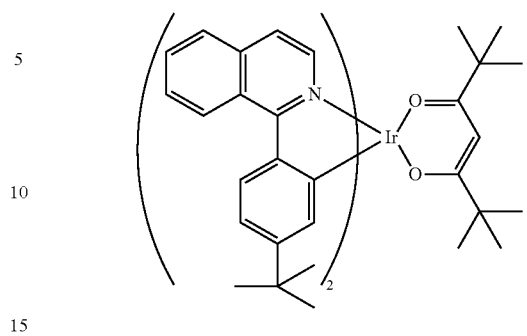
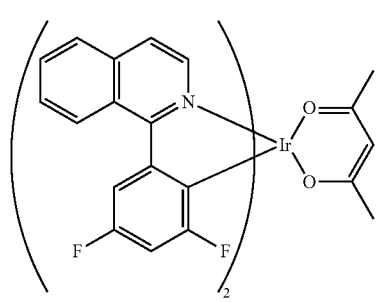
Some non-limiting examples of iridium complex dopants having green emission are given below.
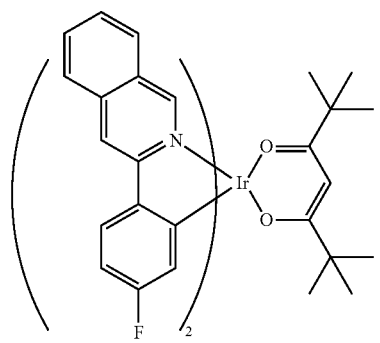
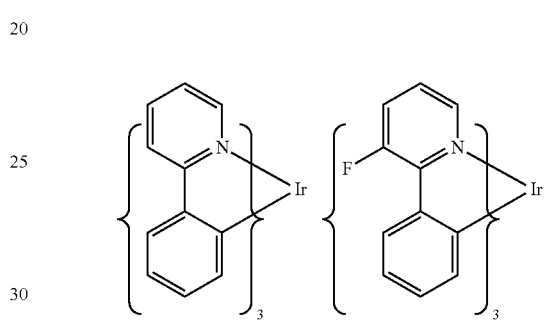
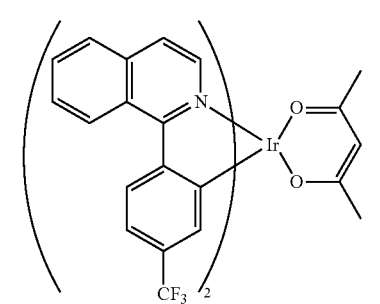
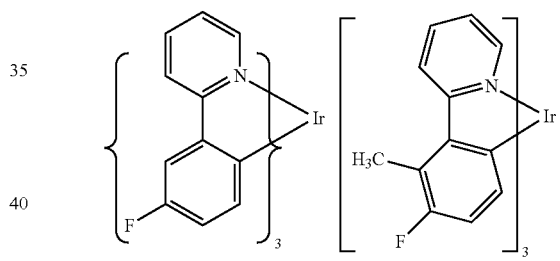
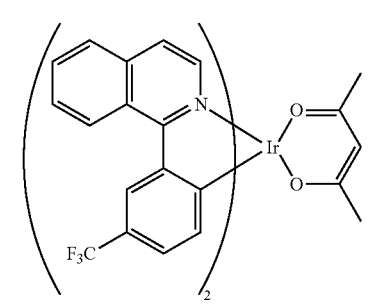
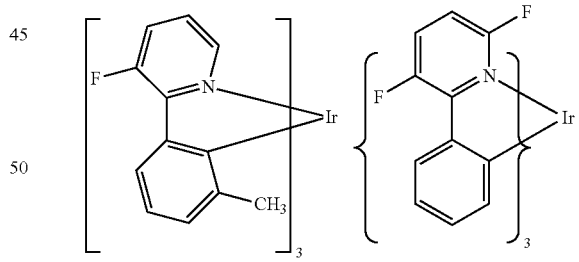
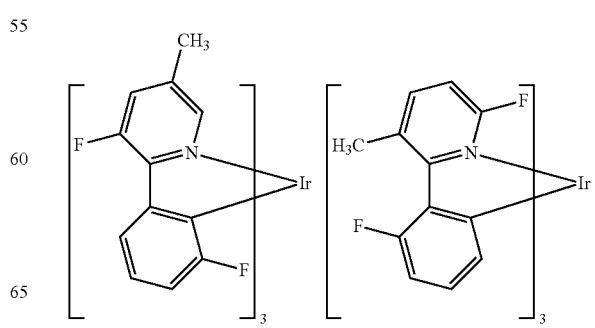

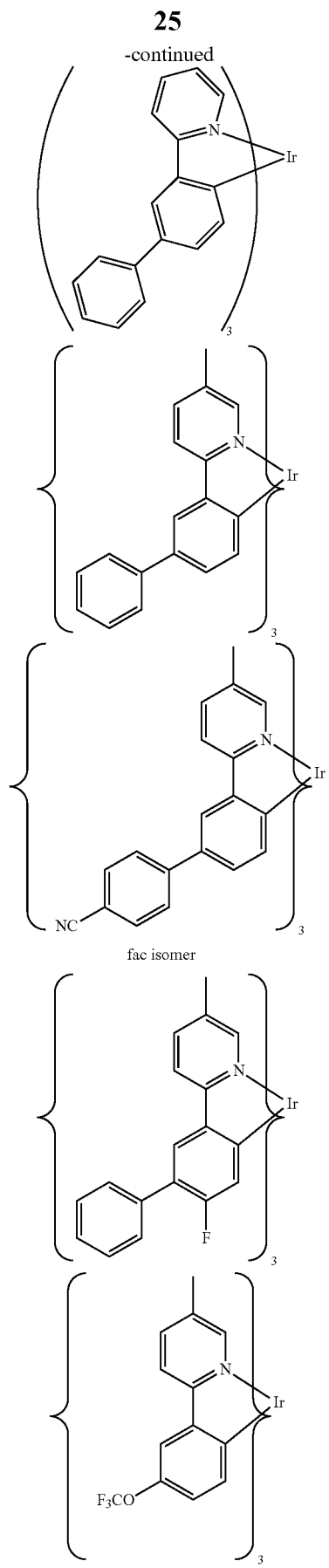
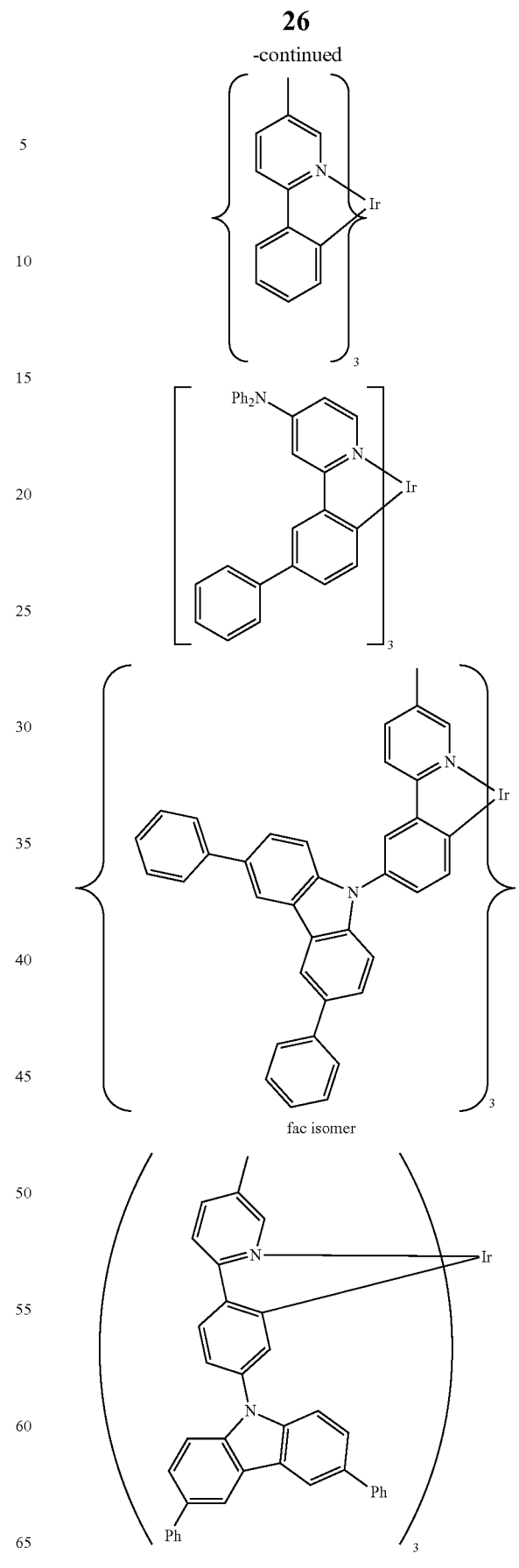

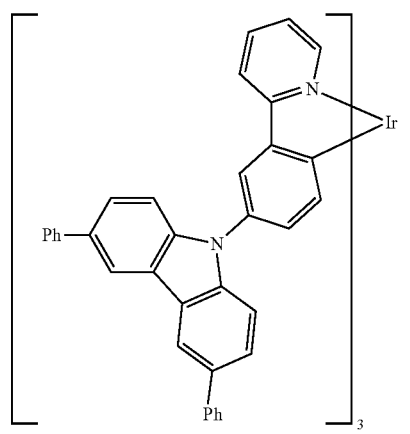
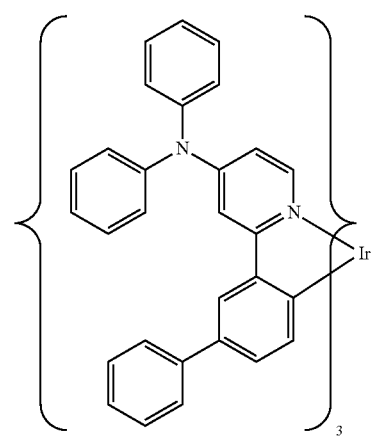
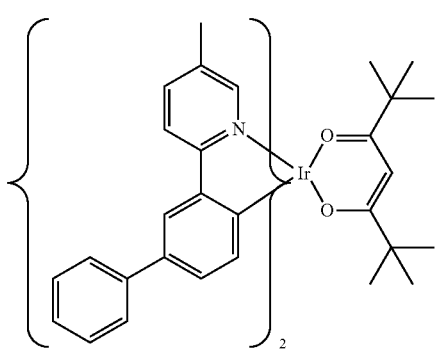
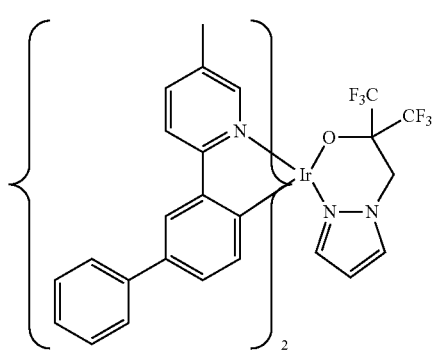
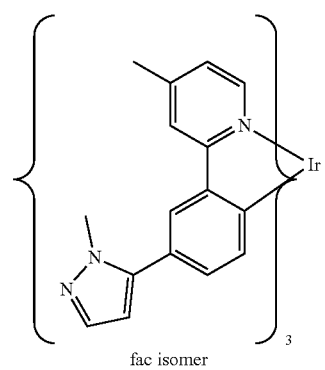
fac isomer
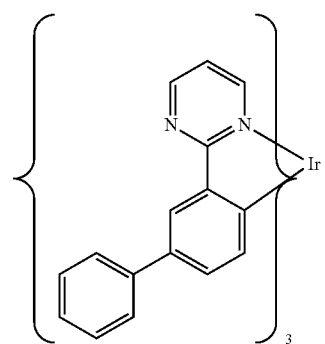
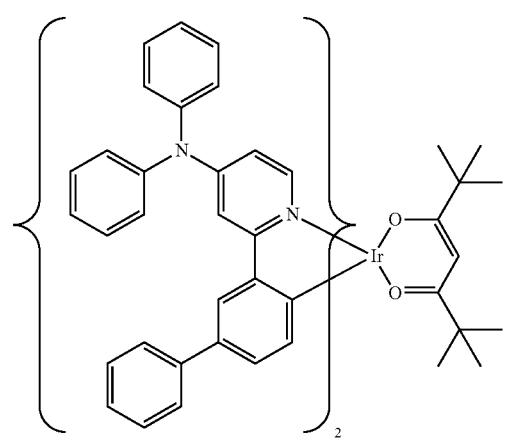
Some non-limiting examples of iridium complex dopants having blue-green to blue emission are given below.
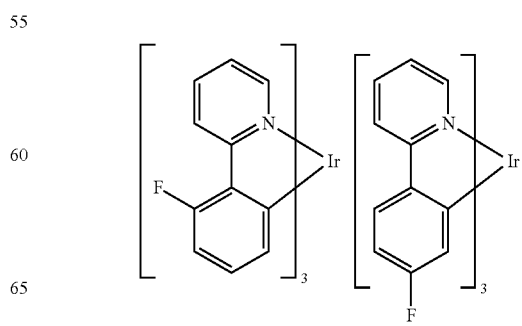

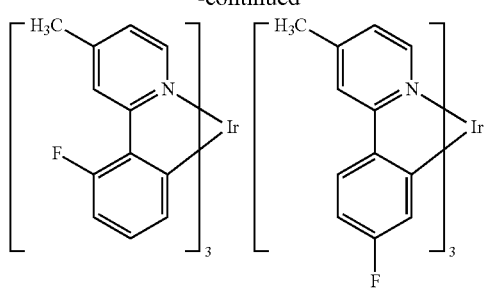
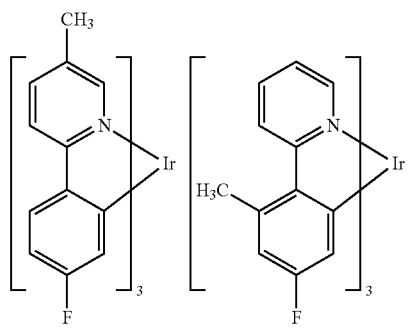
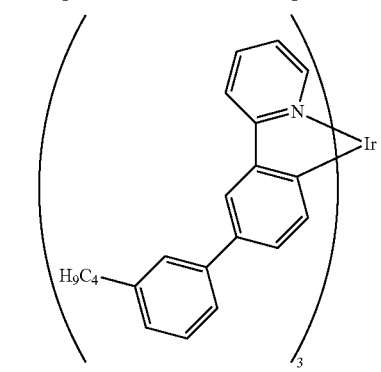
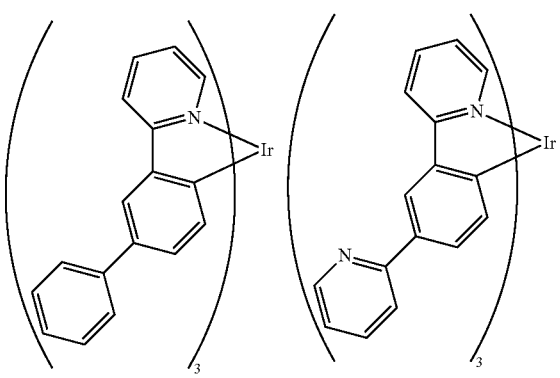
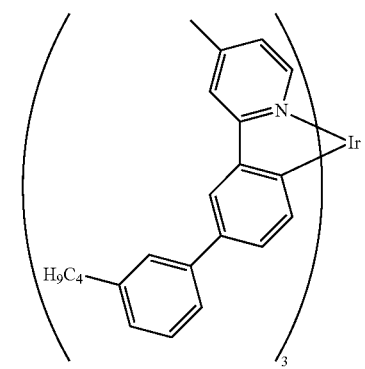
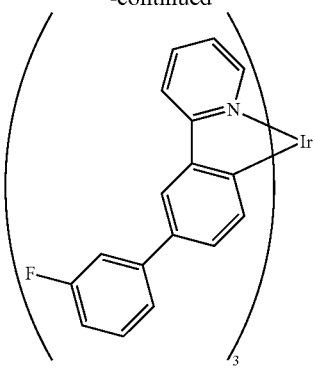
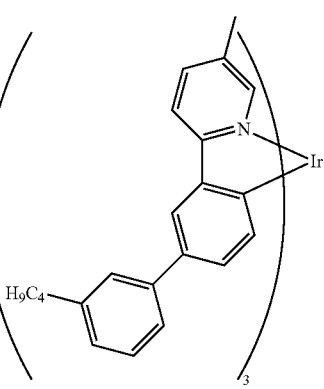
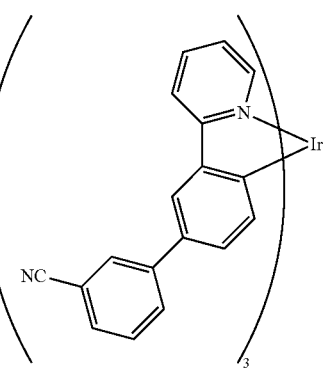
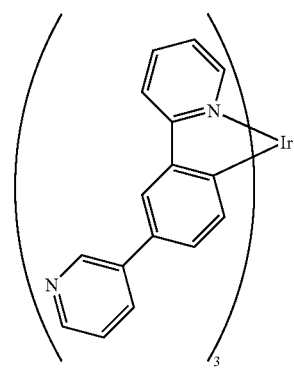

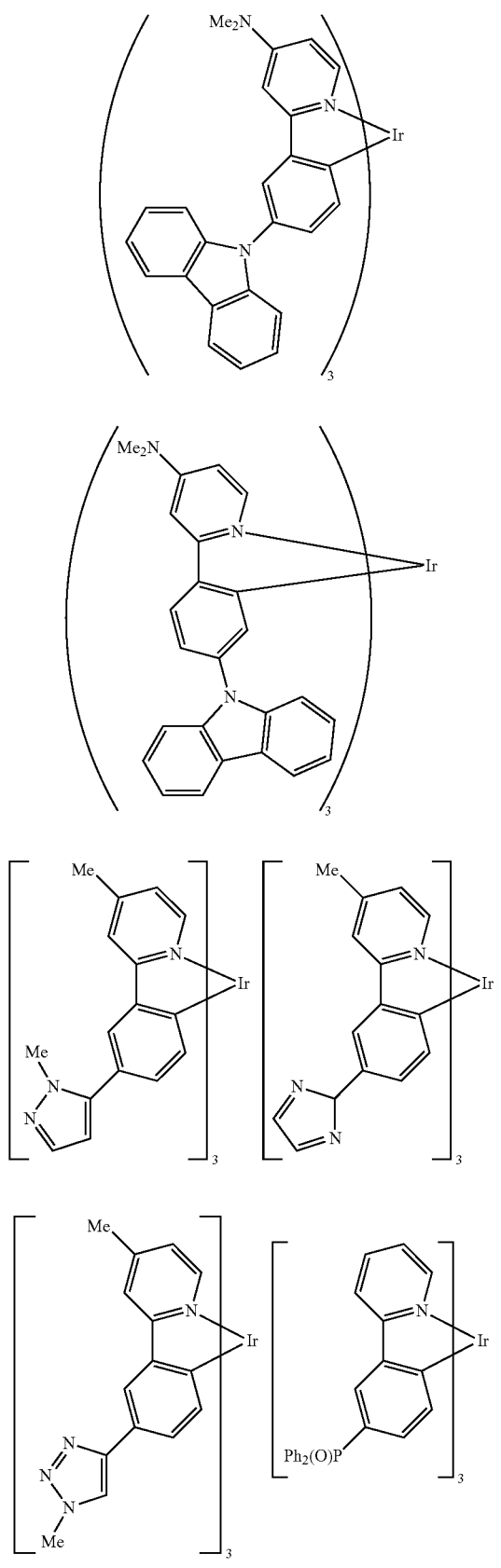
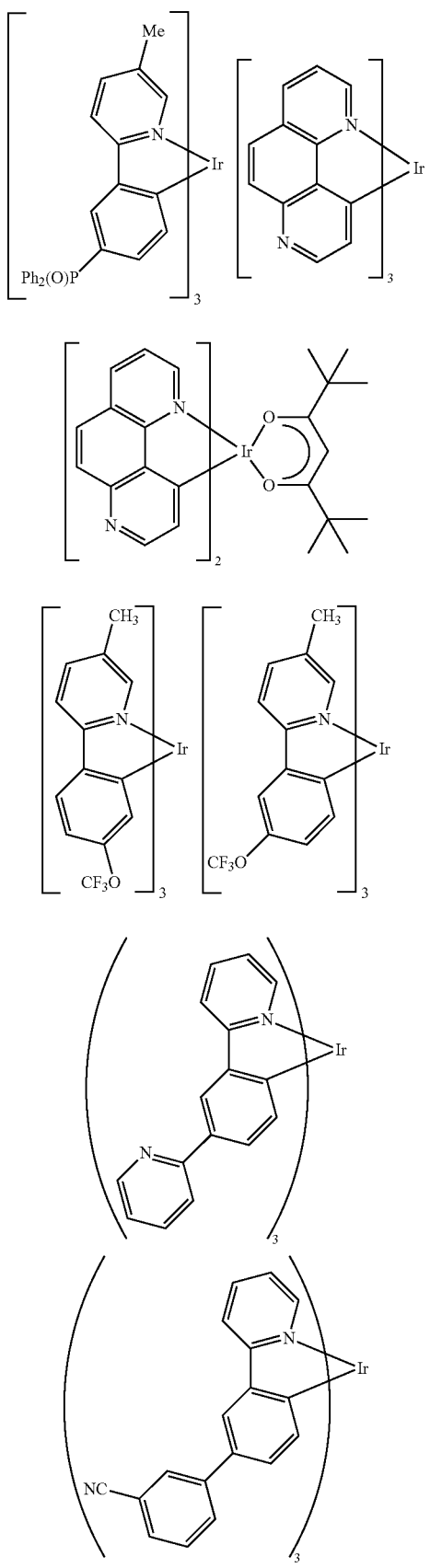

-continued
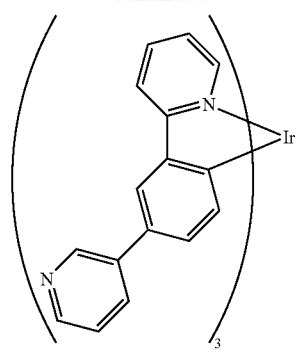
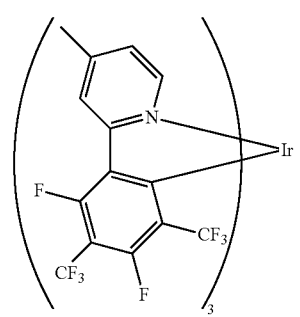
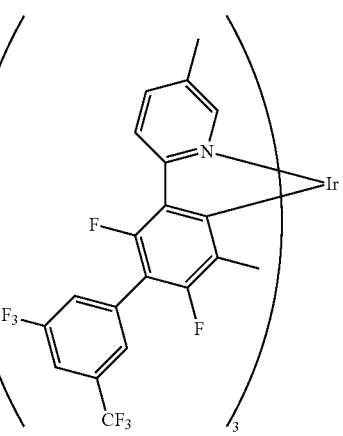
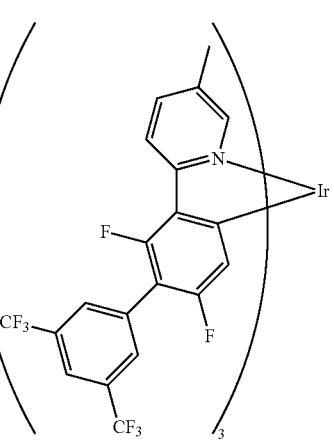
-continued
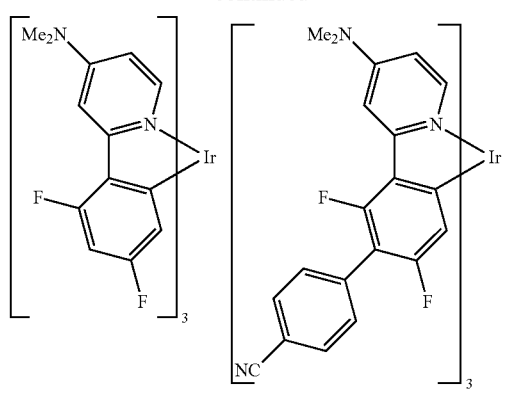
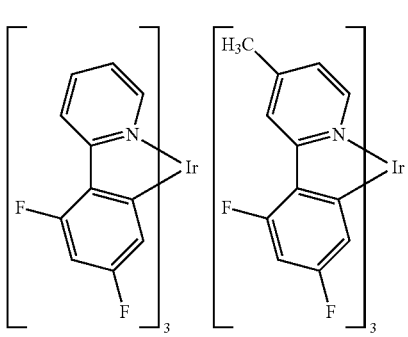
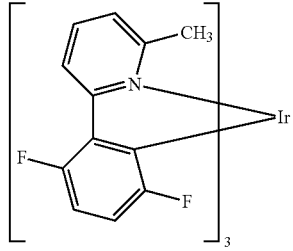
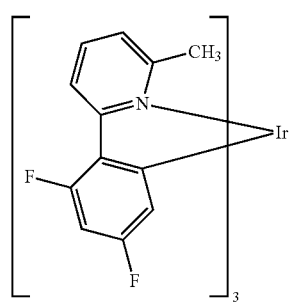
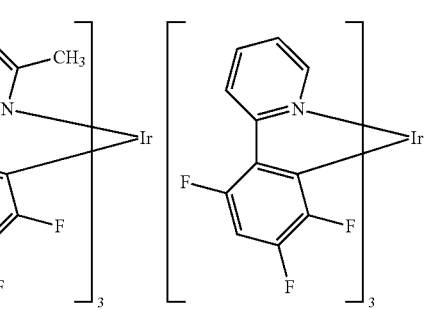

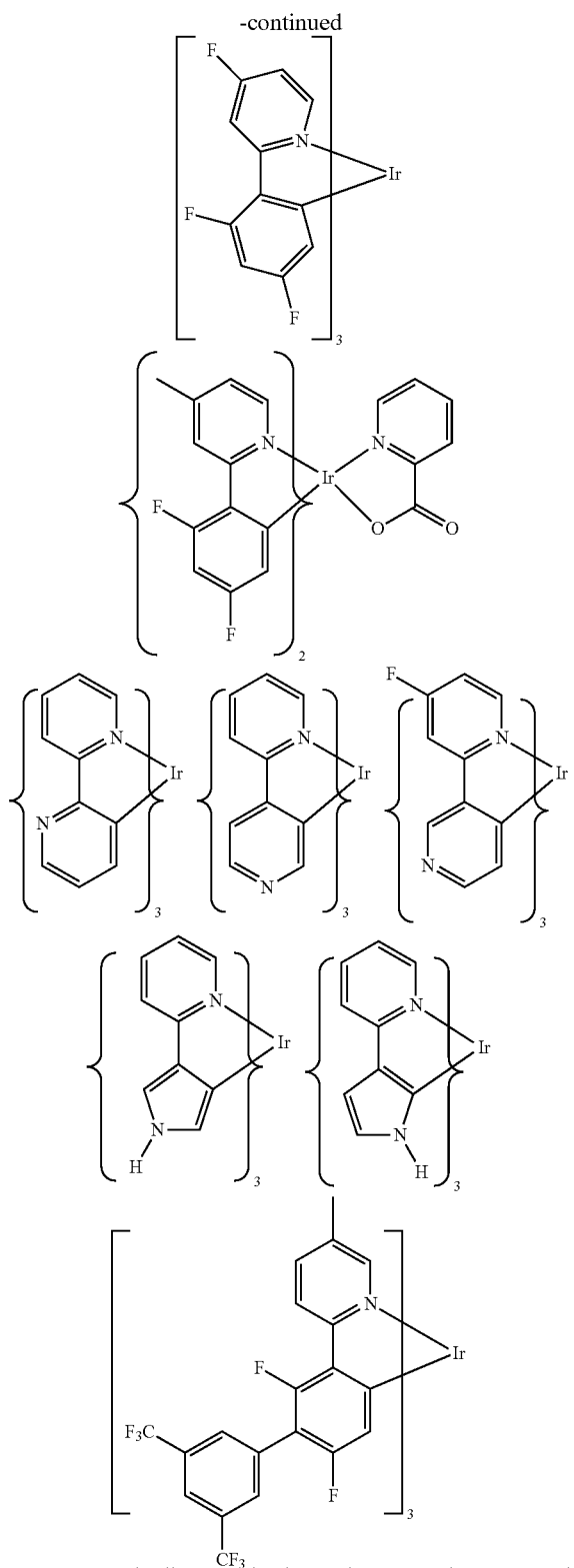

In some embodiments, the dopant is an organic compound. In some embodiments, the dopant is selected from the group consisting of non-polymeric spirobifluorene compounds, fluoranthene compounds, amino-substituted chrysenes and amino-substituted anthracenes.

c. Other Device Layers

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," Nature vol. 357, pp 477-479 (11 Jun. 1992). At least one of the anode and cathode is desirably at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules. They may be vapour deposited or deposited from liquids which may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer. Such materials have been described in, for example, published U.S. patent applications US 2004/0102577, US 2004/0127637, and US 2005/0205860, and published PCT application WO 2009/018009.

Examples of electron transport materials which can be used in the electron transport layer 150, include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport material is selected from the group consisting of metal quinolates and phenanthroline derivatives. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio) tetrathiafulvalene, heterocyclic radicals or diradicals, and the dimers, oligomers, polymers, dispiro compounds and polycycles of heterocyclic radical or diradicals. Layer 150 can function both to facilitate electron transport, and also serve as a buffer layer or confinement layer to prevent quenching of the exciton at layer interfaces. Preferably, this layer promotes electron mobility and reduces exciton quenching.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li- or Cs-containing organometallic compounds, LiF, CsF, and Li$_2$O can also be deposited between the organic layer and the cathode layer to lower the operating voltage.

It is known to have other layers in organic electronic devices. For example, there can be a layer (not shown) between the anode 110 and hole injection layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like.

The present invention also relates to an electronic device comprising at least one active layer positioned between two electrical contact layers, wherein the at least one active layer of the device includes the triarylamine compound of Formula I, II or III. Devices frequently have additional hole transport and electron transport layers.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices made with the anthracene compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The following examples illustrate certain features and advantages of the present invention. They are intended to be illustrative of the invention, but not limiting. All percentages are by weight, unless otherwise to indicated.

Example 1

This example illustrates the increase in triplet energy for the triarylamine compounds described herein. The reference compound is triphenylamine, with a triplet energy of 3.12 eV. The triplet energy of TAPC has been reported as 2.87 eV.

All calculations were performed with the density functional theory (DFT) methods within the Gaussian 03 suite of programs. (*Gaussian* 03, revision D.01; Gaussian, Inc., Wallingford, Conn., 2004). The molecular structures were first optimized at the BP86/6-31G+IrMWB60 level and then used in subsequent analytic vibrational frequency calculations at this same level of computation to ensure that these structures were indeed equilibrium ones. For the excited-state calculations, previous experience has shown that time-dependent DFT (TDDFT) at the B3LYP/6-31G+IrMWB60 level is satisfactory in computing the first seven singlet and triplet energy transitions. In order to obtain HOMO and LUMO values for these molecules, the B3LYP/6-31+G(d)+IrMWB60 level was used.

The computation results are shown in Table 1 below.

TABLE 1

| Computation Results | | | | | |
|---|---|---|---|---|---|
| Structure | HOMO (eV) | LUMO (eV) | H-L$_{gap}$ (eV) | 1$^{st}$ Sing. (eV) | 1$^{st}$ Trip. (eV) |
| 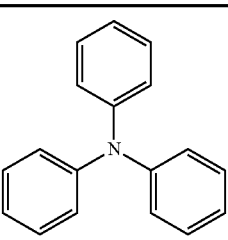 | −5.24 | −0.87 | 4.37 | 3.92 (317 nm) | 3.12 (398 nm) |

TABLE 1-continued

| Structure | HOMO (eV) | LUMO (eV) | H-L$_{gap}$ (eV) | 1$^{st}$ Sing. (eV) | 1$^{st}$ Trip. (eV) |
|---|---|---|---|---|---|
| (structure) | −5.28 | −0.83 | 4.45 | 3.99 (311 nm) | 3.14 (395 nm) |
| (structure) | −5.31 | −0.76 | 4.55 | 4.06 (305 nm) | 3.16 (393 nm) |
| (structure) | −5.31 | −0.75 | 4.56 | 4.07 (305 nm) | 3.25 (382 nm) |
| (structure) | −5.63 | −0.71 | 4.92 | 4.34 (286 nm) | 3.44 (361 nm) |
| (structure) | −6.17 | −0.75 | 5.42 | 4.71 (263 nm) | 3.54 (350 nm) |
| (structure) | −5.35 | −1.05 | 4.30 | 3.91 (317 nm) | 3.05 (407 nm) |

TABLE 1-continued

Computation Results

| Structure | HOMO (eV) | LUMO (eV) | H-L$_{gap}$ (eV) | 1$^{st}$ Sing. (eV) | 1$^{st}$ Trip. (eV) |
|---|---|---|---|---|---|
| 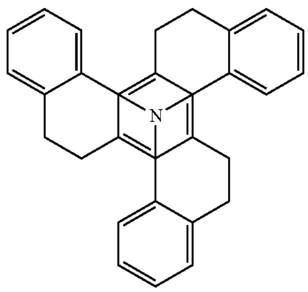 | −5.33 | −0.91 | 4.42 | 3.89 (319 nm) | 3.17 (392 nm) |
| 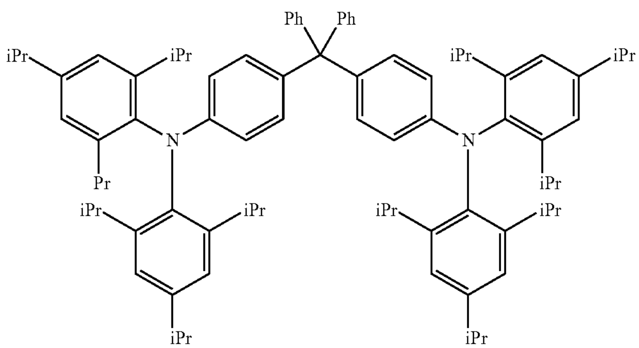 | −5.10 | −0.90 | 4.21 | 3.63 (342 nm) | 3.13 (396 nm) |
| 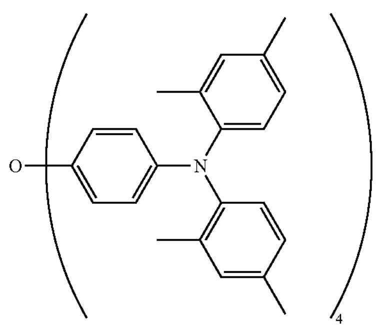 | −4.96 | −0.74 | 4.21 | 3.90 (318 nm) | 3.15 (393 nm) |

Example 2

This example illustrates the preparation of a triarylamine compound having Formula III, 4',4"-(diphenylmethylene)bis(N,N-bis(2,4,5-trimethylphenyl)biphenyl-3-amine), Compound 1.

Compound 1

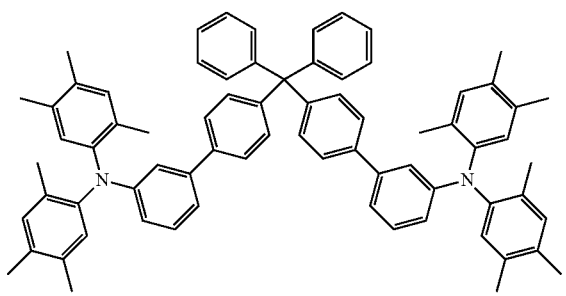

In a dry box, 4',4"-(diphenylmethylene)dibiphenyl-3-amine (0.95 g, 1.80 mmol), 1-bromo-2,4,5-trimethylbenzene (1.52 g, 7.58 mmol), tris(tert-butyl)phosphine (0.029 g, 0.144 mmol) and Pd$_2$(DBA)$_3$ (0.066 g, 0.072 mmol) were combined in round bottom flask and dissolved in 35 ml of dry toluene. The solution was stirred for a minute and followed by sodium tea-butoxide (0.76 g, 7.94 mmol) and 5 ml of dry toluene. A heating mantle was added and the reaction heated to 60 C for 18 hour. The reaction mixture was then cooled to room temperature and filtered, washing with chloroform. The solvent was removed by rotary evaporation and the residue was purified further by silica gel column chromatography using a gradient of chloroform in hexanes (0-36%). The product containing fractions were collected and combined. The solvent was removed by rotary evaporation. The residue was crystallized from dichloromethane and ethanol to give 1.20 g (68%) product as a white powder. 1H NMR (CDCl3) is consistent with the structure for Compound 1.

Example 3

This example illustrates the preparation of a triarylamine compound having Formula III, N,N',N",N'"-(4,4',4", 4'"- methanetetrayltetrakis(benzene-4,1-diyl))tetrakis(2,4,5-trimethyl-N-(2,4,5-trimethylphenyl)aniline), Compound 2.

Compound 2

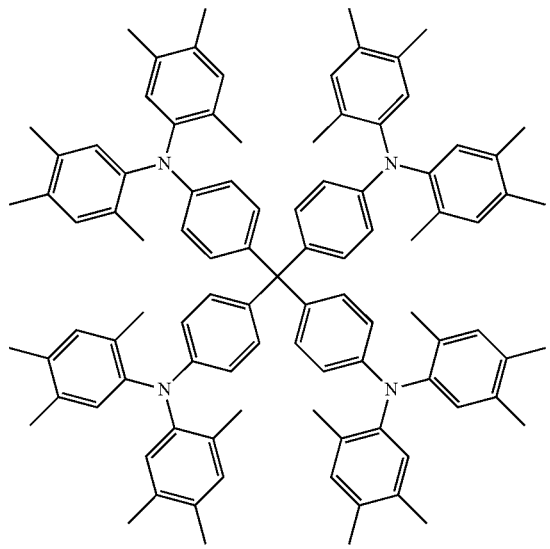

a. tetrakis(4-nitrophenyl)methane

This was prepared according to literature procedures (*J. Am. Chem. Soc.,* 2001, 123 (19), 4432-4445).

To a 250 mL RB flask equipped with a magnetic stirrer and an ice-bath was added fuming nitric acid (45 mL). Tetraphenylmethane (8.21 g, 13.00 mmol) was added slowly with stirring over 15 min at ~0° C. To this reaction was slowly added a mixture of acetic anhydride (14 mL) and acetic acid (28 mL) while maintaining the temperature at ~0° C. The reaction was continued for another 30 min. After which, more acetic acid (55 mL) was added and the mixture was stirred for 15 min. The crude product precipitate was filtered, washed with acetic acid and water, and dried in air. Recrystallization from THF gave 7.22 g (56%) product as white crystals.

b. 4,4',4'',4'''-methanetetrayltetraaniline

To a 250 mL RB flask equipped with a magnetic stirrer and an oil-bath were added tetrakis(4-nitrophenyl)methane (6.50 g, 13.00 mmol), Pd/C (0.98 g, 15 wt %) and n-butanol (150 mL). With nitrogen bubbled through, the mixture was stirred and heated at 50° C. for 15 min. Hydrazine hydrate ((7.6 mL, 156 mmol) was added dropwise via addition funnel while maintaining temperature at 50-60° C. The addition was finished in 30 min. After which, the reaction was stirred at 50° C. for another 2 hr. The reaction remained heterogeneous throughout the time. HPLC analysis indicated all starting material had been consumed and the product appeared as the exclusive component. After cooling to RT, the mixture was purged with nitrogen for 10 min, then filtered and rinsed with THF. The solvent was removed by rotary evaporation and the residue was crystallized from ethanol to give product as light beige crystals, 3.76 g (76%). MS and NMR results are consistent with the structure proposed.

c. N,N',N'',N'''-(4,4',4'',4'''-methanetetrayltetrakis(benzene-4,1-diyl))tetrakis(2,4,5-trimethyl-N-(2,4,5-trimethylphenyl)aniline)

In a dry box, 4,4',4'',4'''-methanetetrayltetraaniline (1.00 g, 3.08 mmol), 1-bromo-2,4,5-trimethylbenzene (1.35 g, 3.67 mmol), tris(tert-butyl)phosphine (0.10 g, 0.50 mmol) and Pd$_2$(DBA)$_3$ (0.23 g, 0.25 mmol) were combined in round bottom flask and dissolved in 120 ml of dry toluene. The solution was stirred for a minute and followed by sodium tert-butoxide (2.72 g, 28.33 mmol) and 5 ml of dry toluene. A heating mantle was added and the reaction heated to 80 C for 18 hour. More 1-bromo-2,4,5-trimethylbenzene (350 mg) and NaOtBu (180 mg) were added and the reaction stirred at 80 C for another 24 hour. The reaction mixture was then cooled to room temperature and filtered, washing with toluene (200 mL). The solvent was removed by rotary evaporation and the residue was re-dissolved in chloroform (40 mL). The crude product was precipitated into methanol (300 mL) and collected (3.3 g, 85% pure) by filtration. The crude product was purified further by silica gel column chromatography using a gradient of chloroform in hexanes (5-21%). Recrystallization from chloroform and ethanol yielded 2.60 g (64%) of product as a pale yellow solid. 1H NMR (CDCl3) is consistent with structure for Compound 2.

Example 4

This example illustrates the preparation of a triarylamine compound having Formula III, N,N'-(4,4'-(cyclohexane-1,1-diyl)bis(4,1-phenylene))bis(2,4,5-trimethyl-N-(2,4,5-trimethylphenyl)aniline), Compound 3.

Compound 3

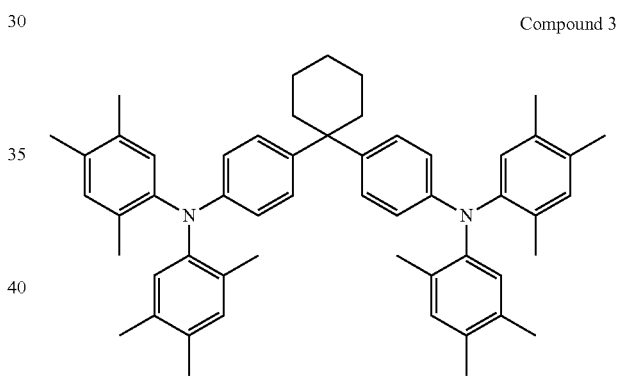

a. 4,4'-(cyclohexane-1,1-diyl)bis(4,1-phenylene)bis(trifluoromethane-sulfonate)

To a 1 L 3-necked RB flask equipped with a magnetic stirrer an addition funnel were added 4,4'-(diphenylmethylene)diphenol (30.00 g), DCM (350 mL) and pyridine (38.00 mL). The original heterogeneous mixture became homogenous after stirring at ambient temperature for 10 min. The flask was then placed in an ice-bath, and trifluoromethane sulfonic anhydride (39.50 mL in 50 mL of DCM was added dropwise (fuming) with stirring in 25 min. After which, the reaction was stirred at ambient temperature for 1 hr. HPLC analysis indicated that all starting material had been consumed and the product appeared as an exclusive component. The solution was washed with diluted HCl (10%, 2×200 mL), water (200 mL) and saturated brine (200 mL). The solution was then stirred with MgSO$_4$ (20 g) at ambient temperature for 1 hour. The mixture was filtered through a short Silica gel column eluted with DCM. The solvent was removed by rotary evaporation and the residue oil crystallized on standing at ambient temperature. The material was collected and dried in a vacuum oven at ambient temperature overnight. Yield, 57.8 g (97%) with a purity of 99% by HPLC analysis.

b. 4,4'-(cyclohexane-1,1-diyl)bis(N-(diphenylmethylene)aniline)

To a 1000 mL RB flask equipped with magnetic stirrer and condenser which was attached to a nitrogen line, were added 4,4'-(cyclohexane-1,1-diyl)bis(4,1-phenylene)bis(trifluoromethanesulfonate) (18.22 g, 34.22 mmol), 4,4'-(cyclohexane-1,1-diyl)bis(4,1-phenylene)bis(trifluoromethanesulfonate) (14.88 g, 82.12 mmol), $Pd_2(OCOCH_3)_2$ (0.46 g, 2.05 mmol), BINAP (1.92 g, 3.08 mmol), $Cs_2CO_3$ (31.22 g, 95.82 mmol) and THF (250 mL). The mixture was bubbled with nitrogen for 15 min through a glass tube from the side arm while the system was purged with nitrogen from the nitrogen line. After which, the mixture was stirred and heated at 80° C. (oil bath) under nitrogen overnight (18 h). After cooling, toluene (300 mL) was added. The solution was washed with water (2×200 mL), saturated brine (100 mL) and dried with $MgSO_4$ at ambient temperature for 4 hour. The solvent was removed by rotary evaporation to give a thick brown oil, which was separated by chromatography on Silica gel column eluted with DCM/Hexance gradient (1/4, 1/1 and 1/0). The product containing fractions were combined, and the solvent was removed by rotary evaporation to give a light-brown thick oil. Methanol (500 mL) was added to the thick oil and the mixture was stirred at ambient condition for 2 hr. During the time a large quantity of white precipitate was formed. The product was collected by filtration, washed with methanol and dried in air. Yield, 14.1 g (69.3%) with a Purity of 95% by HPLC analysis.

c. 4,4'-(cyclohexane-1,1-diyl)dianiline

To above solid (14.0 g, 23.54 mmol) in a 1 L round bottom flask was added THF (200 mL) with stirring. Aqueous HCl (2.5 M, 40 mL) was added slowly. The mixture was stirred at RT for 10 min. The solution was then extracted with ether (200 mL). The aqueous layer was separated and made alkaline with addition of NaOH and extracted with ether (2×150 mL). The ether extracts were combined, washed with saturated brine and dried with $MgSO_4$ at ambient temperature for 3 h. After filtering, the solvent was removed by rotary evaporation to give a light-brown oil. The crude product was separated on Silica gel column eluted with hexane/DCM gradient (1/1, 1/0) first, then with MeOH/DCM (1/9). The product containing fractions were collected and the solvent was removed by rotary evaporation to give a colorless thick oil. Crystallization with DCM/hexane gave the product as light yellow crystalline material. Yield, 5.75 g (90%). NMR spectra are consistent with the structure of the product.

d. N,N'-(4,4'-(cyclohexane-1,1-diyl)bis(4,1-phenylene))bis(2,4,5-trimethyl-N-(2,4,5-trimethylphenyl)aniline)

In a dry box, 4,4'-(cyclohexane-1,1-diyl)dianiline (6.75 g, 25.09 mmol), 1-bromo-2,4,5-trimethylbenzene (21.19 g, 105.36 mmol), tris(tert-butyl)phosphine (0.41 g, 2.01 mmol) and $Pd_2(DBA)_3$ (0.92 g, 1.00 mmol) were combined in round bottom flask and dissolved in 450 ml of dry toluene. The solution was stirred for a minute and followed by sodium tert-butoxide (10.61 g, 110.38 mmol) and 50 ml of dry toluene. A heating mantle was added and the reaction heated to 80 C for 18 hour. The reaction mixture was then cooled to room temperature and filtered, washing with chloroform. The solvent was removed by rotary evaporation and the residue was purified further by silica gel column chromatography using a gradient of chloroform in hexanes (0-25%). The product containing fractions were collected and combined. The solvent was removed by rotary evaporation. The crude product was dissolved in DCM (100 mL) and precipitated into methanol (700 mL) to give 17.47 g (94%) product as a white powder. 1H NMR (CDCl3) is consistent with structure.

Example 5

This illustrates the preparation of a triarylamine compound having Formula III, N,N'-(4,4'-(1-phenylethane-1,1-diyl)bis (4,1-phenylene))bis(3'-phenyl-6-methyl-N-(2,4,6-tri isopropylphenyl)biphenyl-3-amine, Compound 4.

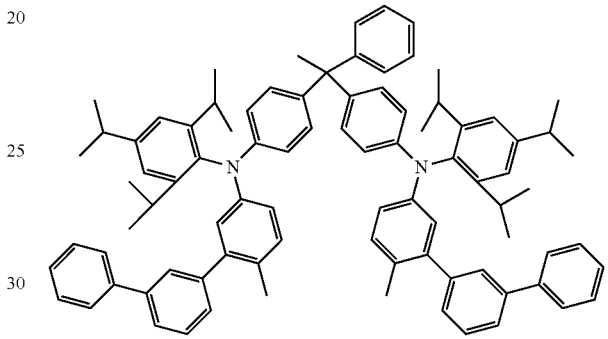

Compound 4

To a 50 mL round bottom flask were added $Pd(OAc)_2$ and S-Phos (0.12 g, 0.29 mmol) and dioxane (10 mL). With stirring, the system was purged with nitrogen for 10 minutes. In a separate flask, water (0.004 g, 0.23 mmol) was mixed with dioxane (2 mL) and purged with nitrogen for 5 minutes then added to the catalyst solution. The mixture was heated at 100 C for a minute whereupon the color darkened from a bright red to a dark black/red.

To a two necked 200 mL round bottom flask, under nitrogen, were added N,N'-(4,4'-(1-phenylethane-1,1-diyl)bis(4, 1-phenylene))bis(2,4,6-triisopropylaniline) (2.02 g, 2.91 mmol), 5- and dioxane (50 mL). With stirring, the system was purged with nitrogen for 10 minutes then the catalyst solution was added. A heating mantle was added and the reaction heated to 110 C under nitrogen for 3 day. The reaction mixture was then cooled to room temperature and filtered, washing with chloroform. The solvent was removed by rotary evaporation and the residue was purified further by silica gel column chromatography using a gradient of chloroform in hexanes (0-31%). The product containing fractions were collected and combined. The solvent was removed by rotary evaporation. The residue was crystallized from dichloromethane and acetonitrile repeatedly to give 0.34 g (10%) of product as a white powder in >99.9% purity by HPLC analysis. 1H NMR (CDCl3) is consistent with structure.

Examples 6-8 and Comparative Examples A and B

These examples illustrate the performance of the new triarylamine compounds in a device.
(a) Materials:
HIJ-1 is an aqueous dispersion of an electrically conductive polymer and a polymeric fluorinated sulfonic acid. Such materials have been described in, for example, published U.S. patent applications US 2004/0102577, US 2004/0127637, and US 2005/0205860, and published PCT application WO 2009/018009.

TAPC is 1,1-bis[(di-4-tolylamino)phenyl]cyclohexane, shown below.

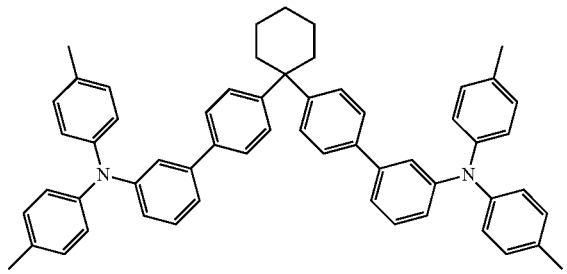

NPB is N,N'-bis(naphthalen-1-yl)-N,N'-bis-(phenyl)benzidine, shown below

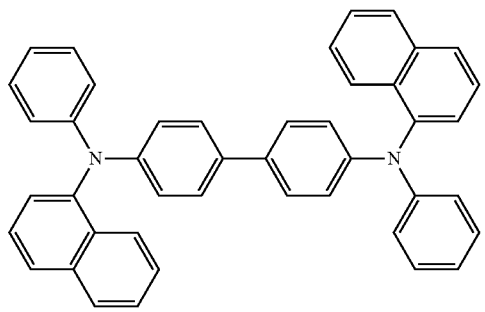

Green-1 is an organometallic Ir emitter having the structure shown below.

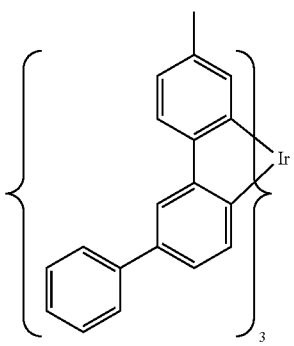

Host-1 is an indolocarbazole derivative shown below. Such materials have been described in published European patent application EP 2080762.

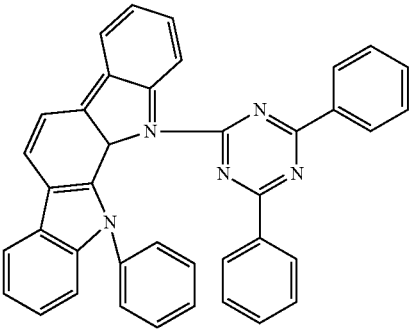

ET-1 is a triphenylene derivative.
ET-2 is a metal quinolate derivative.

(b) Device

In these examples, devices were made by a combination of solution processing and vapor deposition techniques. A substrate with 80 nm indium tin oxide ("ITO") was used as the anode. HIJ-1 was applied by spin coating from an aqueous dispersion. The other materials were applied by evaporative deposition. The device structure was:

anode: ITO (80 nm)
hole injection layer: HIJ-1 (60 nm)
hole transport layer: materials shown in Table 2 (20 nm)
electroactive layer: 10% Green-I in Host-1 (66 nm)
first electron transport layer: ET-1 (5 nm)
second electron transport layer: ET-2 (15 nm)
electron injection layer: LiF (1 nm deposited)
cathode: Al (100 nm)

In Example 6, the hole transport material is Compound 3.
In Example 7, the hole transport material is Compound 4.
In Example 8, the hole transport material is Compound 1.
In Comparative Example A, the hole transport material is TAPC.
In Comparative Example B, the hole transport material is NPB.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The external quantum efficiency (EQE) is then calculated from the current efficiency (cd/A) and the electroluminance spectra, assuming a Lambertian distribution of emitted light. The results are shown in Table 2.

TABLE 2

Device Results

| Example | HTL | External Quantum efficiency @1000 nits | Current efficiency @1000 nits | Color (x, y) |
| --- | --- | --- | --- | --- |
| Comparative A | TAPC | 21% | 77 cd/A | (0.337, 0.634) |
| Comparative B | NPB | 17.9% | 66.7 cd/A | (0.32, 0.647) |
| Example 6 | Compound 3 | 23% | 86 cd/A | (0.331, 0.638) |
| Example 7 | Compound 4 | 23.7% | 90 cd/A | (0.323, 0.644) |
| Example 8 | Compound 1 | 22.5% | 84 cd/A | (0.327, 0.64) |

HTL = hole transport layer; x and y are the color coordinates according to the C.I.E. chromaticity scale (Commission Internationale de L'Eclairage, 1931).

The external quantum efficiency and the current efficiency are greater with the new triarylamine compounds of the invention.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound selected from the group consisting of

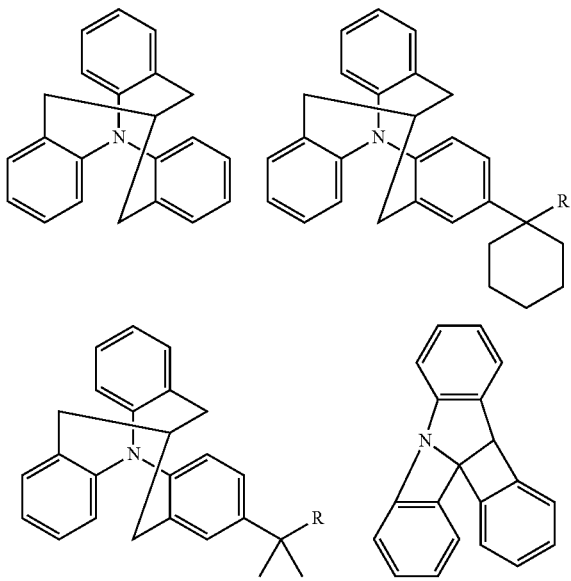

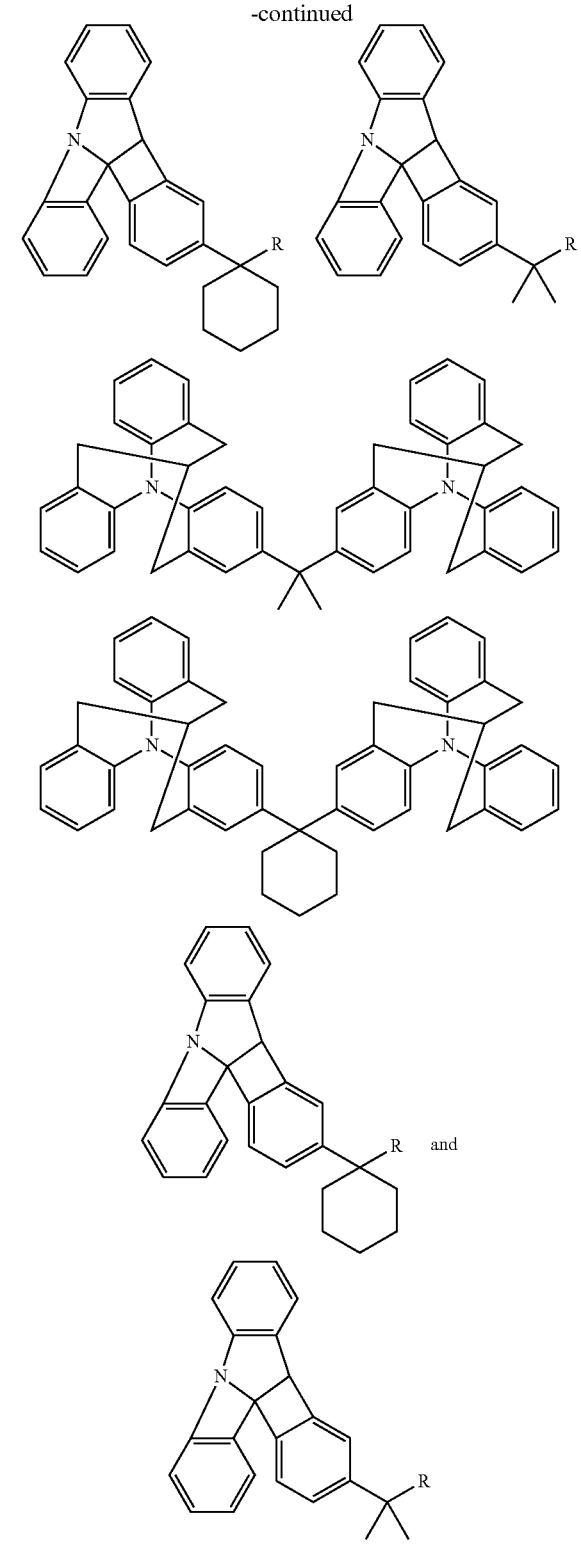

where R is a group selected from alkyl groups and aryl groups.

2. The compound of claim 1, which is at least 10% deuterated.

3. The compound of claim 1, which is at least 50% deuterated.

4. The compound of claim 1, which is 100% deuterated.

5. The compound of claim 1, wherein the alkyl group has 1-3 carbon atoms.

6. The compound of claim 1, wherein the aryl group is selected from the group consisting of phenyl, biphenyl, naphthyl, deuterated derivatives thereof, and a group having Formula IV:

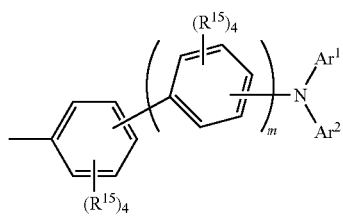

Formula IV where:
- $Ar^1$ and $Ar^2$ are the same or different and are aryl groups, or $Ar^1$ and $Ar^2$ can be joined together to form a carbazole group;
- $R^{15}$ is the same or different at each occurrence and is selected from the group consisting of H, D, and alkyl, or adjacent $R^{15}$ groups may be joined together to form an aromatic ring; and
- m is the same or different at each occurrence and is an integer from 0 to 5.

7. An electroactive composition comprising:
(a) a triarylamine compound host selected from the group consisting of

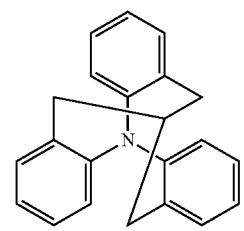
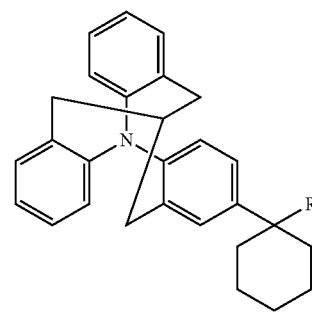
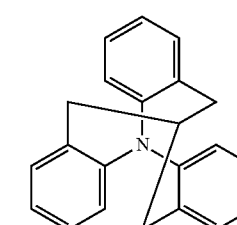
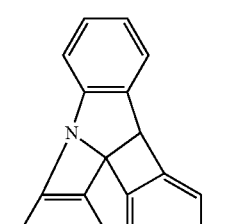
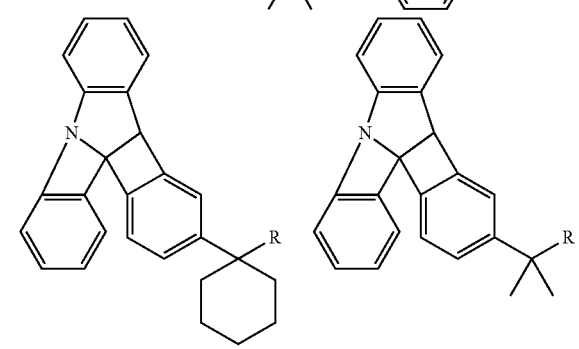

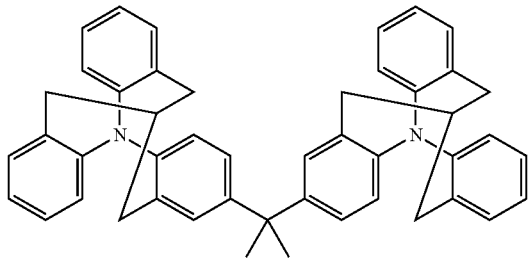
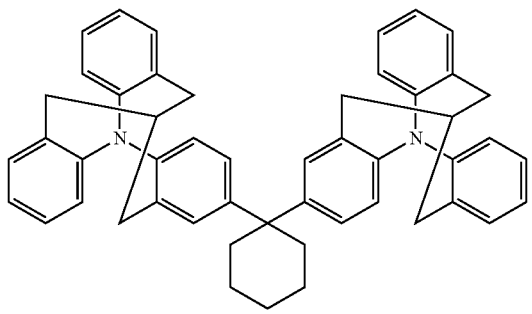
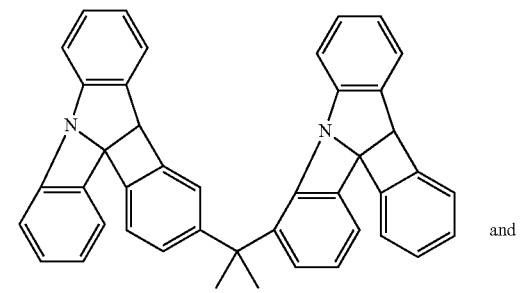
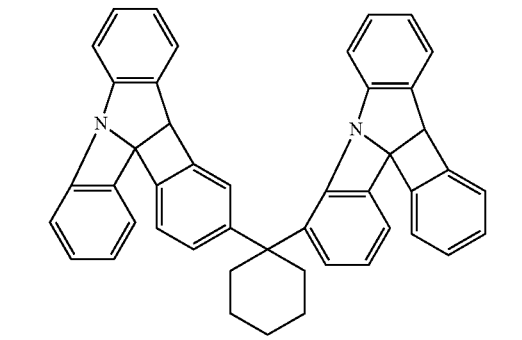
and
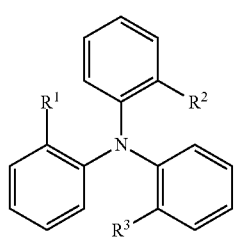

where R is a group selected from alkyl groups and aryl groups

Formula I

Formula II

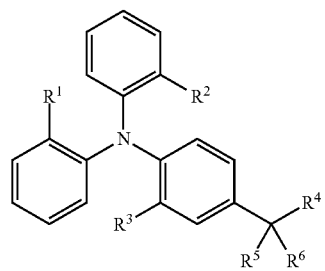

Formula III

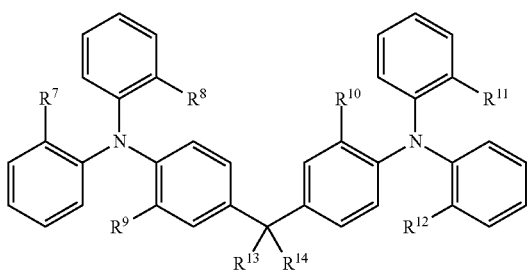

; and
(b) an organometallic dopant capable of electroluminescence having an emission maximum between 380 and 750 nm;
wherein the electroactive composition is light-emitting.

8. The electroactive composition of claim 7, which further comprises: (c) a second host material.

9. The electroactive composition of claim 8, wherein the second host material is selected from the group consisting of chrysenes, phenanthrenes, triphenylenes, phenanthrolines, naphthalenes, anthracenes, quinolines, isoquinolines, quinoxalines, phenylpyridines, benzodifurans, indolocarbazoles, and metal quinolinate complexes.

10. An organic electronic device comprising a first electrical contact layer, a second electrical contact layer, and at least one active layer therebetween, wherein the active layer comprises a compound selected from the group consisting of:

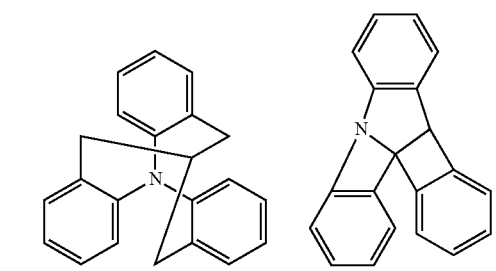

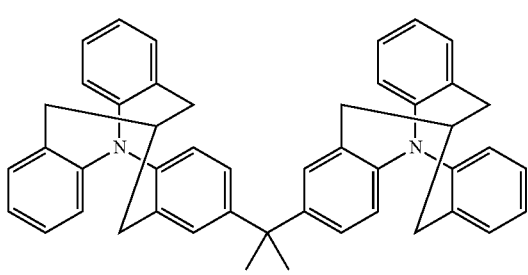

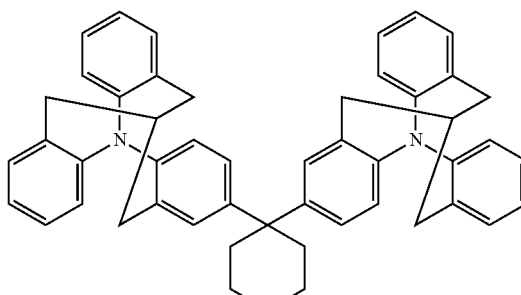

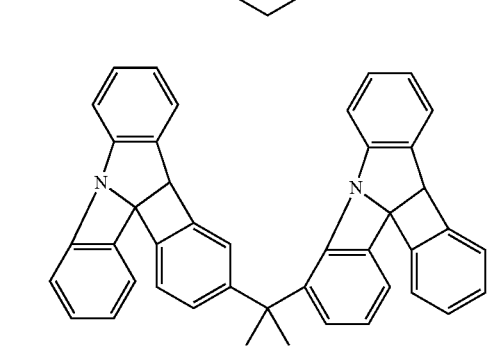

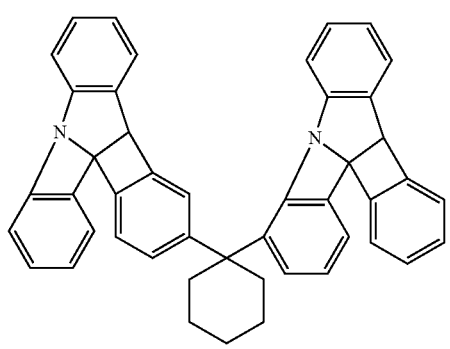

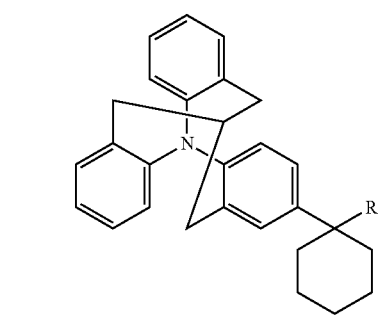

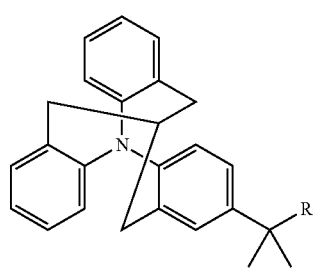

-continued

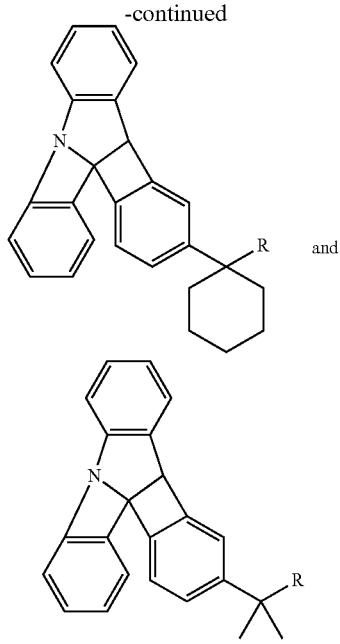

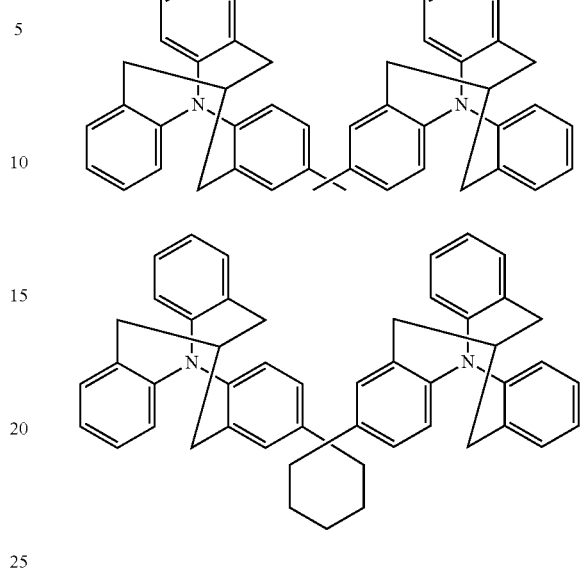

where R is a group selected from alkyl groups and aryl groups.

11. The device of claim 10, further comprising a hole injection layer between the first electrical contact layer and the active layer, wherein the hole injection layer comprises at least one electrically conductive polymer and at least one fluorinated acid polymer.

12. The device of claim 10, wherein the active layer is a hole transport layer.

13. The device of claim 10, wherein the active layer is a light-emitting layer and further comprises an organometallic dopant capable of electroluminescence having an emission maximum between 380 and 750 nm.

14. The device of claim 10, wherein the compound is selected from the group consisting of:

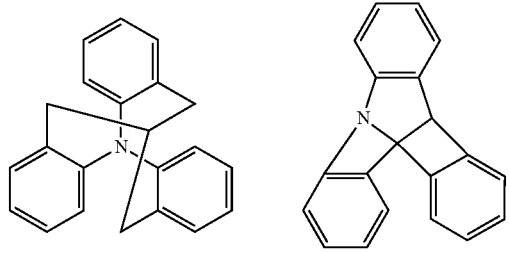

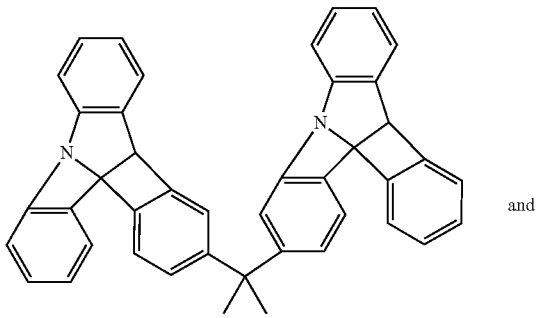

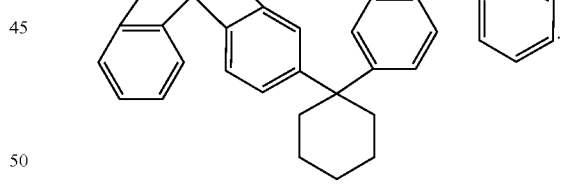

* * * * *